United States Patent
Gordon et al.

(10) Patent No.: US 8,420,365 B2
(45) Date of Patent: Apr. 16, 2013

(54) 11β HYDROXYSTEROID DEHYDROGENASE TYPE 1

(75) Inventors: David Gordon, Doylestown, PA (US);
Yuval Blat, Wynnewood, PA (US);
Akbar Nayeem, Newtown, PA (US);
Mark S. Kirby, New Hope, PA (US);
Bin He, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 289 days.

(21) Appl. No.: 12/681,916

(22) PCT Filed: Oct. 8, 2008

(86) PCT No.: PCT/US2008/079132
§ 371 (c)(1),
(2), (4) Date: Apr. 7, 2010

(87) PCT Pub. No.: WO2009/048903
PCT Pub. Date: Apr. 16, 2009

(65) Prior Publication Data
US 2010/0209990 A1       Aug. 19, 2010

Related U.S. Application Data

(60) Provisional application No. 60/978,231, filed on Oct. 8, 2007.

(51) Int. Cl.
*C12N 9/02* (2006.01)

(52) U.S. Cl.
USPC ............................ 435/189; 435/183; 530/350

(58) Field of Classification Search ........................ None
See application file for complete search history.

(56) References Cited

U.S. PATENT DOCUMENTS

2003/0198965 A1   10/2003   Freier
2006/0105973 A1   5/2006   Freier

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Walker et al., "Tissue Production of Cortisol by 11β-Hydroxysteroid Dehydrogenase Type 1 and Metaboic Disease", Ann. New York Academy of Sciences, 2006, vol. 1083, pp. 165-184.
Weisgraber, "Apolipoprotein E: Structure-Function Relationships", Advances in Protein Chemistry, 1994, vol. 45, pp. 249-302.

* cited by examiner

*Primary Examiner* — Richard Hutson
(74) *Attorney, Agent, or Firm* — Eve L. Frank

(57) ABSTRACT

The invention provides gene-targeted non-human animals comprising a genetically modified 11βHSD1 gene encodes a mutant 11βHSD1 polypeptide which is modulated by human 11βHSD1 modulating compounds. The invention further provides cells expressing mutant 11βHSD1 and cells isolated from gene-targeted animals, which cells produce a mutant 11βHSD1. The invention further provides methods of identifying agents that modulate 11βHSD1 activity, and are useful to treat 11βHSD1-related metabolic disorders.

2 Claims, 10 Drawing Sheets

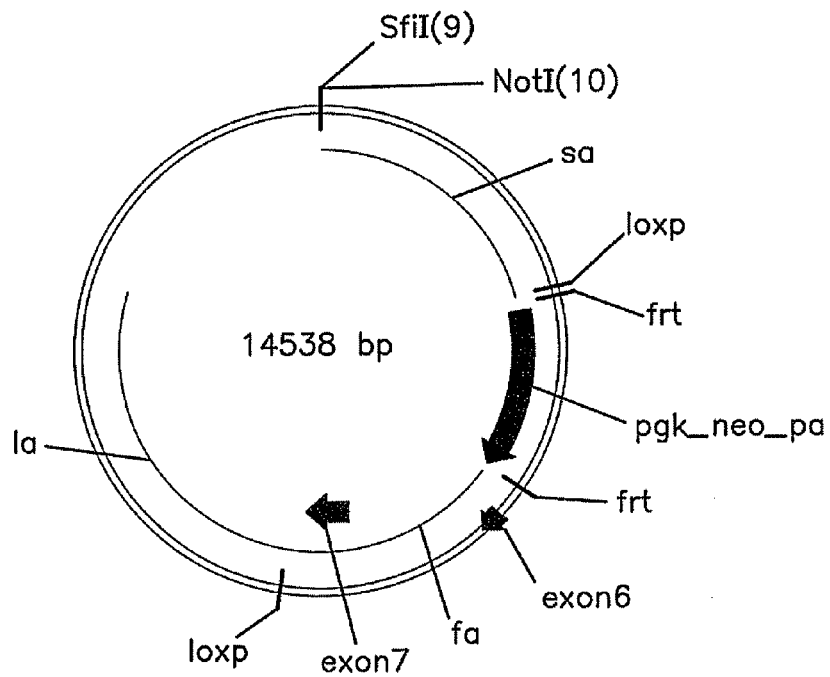
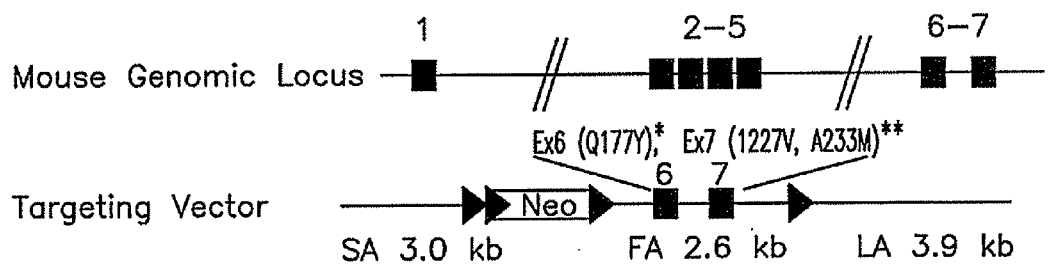
FIG. 1

11βHSD1 human nucleotide sequence

ATGGCTTTTATGAAAAAATATCTCCTCCCCATTCTGGGGCTCTTCATGGCC
TACTACTACTATTCTGCAAACGAGGAATTCAGACCAGAGATGCTCCAAGG
AAAGAAAGTGATTGTCACAGGGGCCAGCAAAGGGATCGGAAGAGAGATG
GCTTATCATCTGGCGAAGATGGGAGCCCATGTGGTGGTGACAGCGAGGTC
AAAAGAAACTCTACAGAAGGTGGTATCCCACTGCCTGGAGCTTGGAGCAG
CCTCAGCACACTACATTGCTGGCACCATGGAAGACATGACCTTCGCAGAG
CAATTTGTTGCCCAAGCAGGAAAGCTCATGGGAGGACTAGACATGCTCAT
TCTCAACCACATCACCAACACTTCTTTGAATCTTTTTCATGATGATATTCAC
CATGTGCGCAAAAGCATGGAAGTCAACTTCCTCAGTTACGTGGTCCTGACT
GTAGCTGCCTTGCCCATGCTGAAGCAGAGCAATGGAAGCATTGTTGTCGT
CTCCTCTCTGGCTGGGAAAGTGGCTTATCCAATGGTTGCTGCCTATTCTGC
AAGCAAGTTTGCTTTGGATGGGTTCTTCTCCTCCATCAGAAAGGAATATTC
AGTGTCCAGGGTCAATGTATCAATCACTCTCTGTGTTCTTGGCCTCATAGA
CACAGAAACAGCCATGAAGGCAGTTTCTGGGATAGTCCATATGCAAGCAG
CTCCAAAGGAGGAATGTGCCCTGGAGATCATCAAGGGGGAGCTCTGCGC
CAAGAAGAAGTGTATTATGACAGCTCACTCTGGACCACTCTTCTGATCAG
AAATCCATGCAGGAAGATCCTGGAATTTCTCTACTCAACGAGCTATAATAT
GGACAGATTCATAAACAAGTAG (SEQ ID NO:1)

11βHSD1 human peptide sequence

MAFMKKYLLPILGLFMAYYYYSANEEFRPEMLQGKKVIVTGASKGIGREM
AYHLAKMGAHVVVTARSKETLQKVVSHCLELGAASAHYIAGTMEDMTFAE
QFVAQAGKLMGGLDMLILNHITNTSLNLFHDDIHHVRKSMEVNFLSYVVL
TVAALPMLKQSNGSIVVVSSLAGKVAYPMVAAYSASKFALDGFFSSIRKE
YSVSRVNVSITLCVLGLIDTETAMKAVSGIVHMQAAPKEECALEIIKGGA
LRQEEVYYDSSLWTTLLIRNPCRKILEFLYSTSYNMDRFINK (SEQ ID NO:2)

FIG. 3

11βHSD1 mouse nucleotide sequence

ATGGCAGTTATGAAAAATTACCTCCTCCCGATCCTGGTGCTCTTCCTGGCC
TACTACTACTATTCTACAAATGAAGAGTTCAGACCAGAAATGCTCCAGGG
AAAGAAAGTGATTGTCACTGGGGCCAGCAAAGGGATTGGAAGAGAAATG
GCATATCATCTGTCAAAAATGGGAGCCCATGTGGTATTGACTGCCAGGTC
GGAGGAAGGTCTCCAGAAGGTAGTGTCTCGCTGCCTTGAACTCGGAGCAG
CCTCTGCTCACTACATTGCTGGCACTATGGAAGACATGACATTTGCGGAGC
AATTTATTGTCAAGGCGGGAAAGCTCATGGGCGGACTGGACATGCTTAT
TCTAAACCACATCACTCAGACCTCGCTGTCTCTCTTCCATGACGACATCCA
CTCTGTGCGAAGAGTCATGGAGGTCAACTTCCTCAGCTACGTGGTCATGA
GCACAGCCGCCTTGCCCATGCTGAAGCAGAGCAATGGCAGCATTGCCGTC
ATCTCCTCCTTGGCTGGGAAAATGACCCAGCCTATGATTGCTCCCTACTCT
GCAAGCAAGTTTGCTCTGGATGGGTTCTTTTCCACCATTAGAACAGAACTC
TACATAACCAAGGTCAACGTGTCCATCACTCTCTGTGTCCTTGGCCTCATA
GACACAGAAACAGCTATGAAGGAAATCTCTGGGATAATTAACGCCCAAGC
TTCTCCCAAGGAGGAGTGCGCCCTGGAGATCATCAAAGGCACAGCTCTAC
GCAAAAGCGAGGTGTACTATGACAAATCGCCTTTGACTCCAATCCTGCTTG
GGAACCCAGGAAGGAAGATCATGGAATTTTTTTCATTACGATATTATAAT
AAGGACATGTTTGTAAGTAACTAG (SEQ ID NO:3)

11βHSD1 mouse peptide sequence

MAVMKNYLLPILVLFLAYYYYSTNEEFRPEMLQGKKVIVTGASKGIGREM
AYHLSKMGAHVVLTARSEEGLQKVVSRCLELGAASAHYIAGTMEDMTFAE
QFIVKAGKLMGGLDMLILNHITQTSLSLFHDDIHSVRRVMEVNFLSYVVM
STAALPMLKQSNGSIAVISSLAGKMTQPMIAPYSASKFALDGFFSTIRTE
LYITKVNVSITLCVLGLIDTETAMKEISGIINAQASPKEECALEIIKGTA
LRKSEVYYDKSPLTPILLGNPGRKIMEFFSLRYYNKDMFVSN (SEQ ID NO:4)

FIG. 4

Single mutant; Q177Y nucleotide sequence
*Changes reflected by bold, italic, and enlarged font.

ATGGCAGTTATGAAAAATTACCTCCTCCCGATCCTGGTGCTCTTCCTGGCC
TACTACTACTATTCTACAAATGAAGAGTTCAGACCAGAAATGCTCCAGGG
AAAGAAAGTGATTGTCACTGGGGCCAGCAAAGGGATTGGAAGAGAAATG
GCATATCATCTGTCAAAAATGGGAGCCCATGTGGTATTGACTGCCAGGTC
GGAGGAAGGTCTCCAGAAGGTAGTGTCTCGCTGCCTTGAACTCGGAGCAG
CCTCTGCTCACTACATTGCTGGCACTATGGAAGACATGACATTTGCGGAGC
AATTTATTGTCAAGGCGGGAAAGCTCATGGGCGGACTGGACATGCTTAT
TCTAAACCACATCACTCAGACCTCGCTGTCTCTCTTCCATGACGACATCCA
CTCTGTGCGAAGAGTCATGGAGGTCAACTTCCTCAGCTACGTGGTCATGA
GCACAGCCGCCTTGCCCATGCTGAAGCAGAGCAATGGCAGCATTGCCGTC
ATCTCCTCCTTGGCTGGGAAAATGACC*TAT*CCTATGATTGCTCCCTACTCT
GCAAGCAAGTTTGCTCTGGATGGGTTCTTTTCCACCATTAGAACAGAACTC
TACATAACCAAGGTCAACGTGTCCATCACTCTCTGTGTCCTTGGCCTCATA
GACACAGAAACAGCTATGAAGGAAATCTCTGGGATAATTAACGCCC
AAGCTTCTCCCAAGGAGGAGTGCGCCCTGGAGATCATCAAAGGCACAGCT
CTACGCAAAAGCGAGGTGTACTATGACAAATCGCCTTTGACTCCAATCCT
GCTTGGGAACCCAGGAAGGAAGATCATGGAATTTTTTTCATTACGATATTA
TAATAAGGACATGTTTGTAAGTAACTAG (SEQ ID NO: 5)

Single mutant: Q177Y peptide sequence

MAVMKNYLLPILVLFLAYYYYSTNEEFRPEMLQGKKVIVTGASKGIGREM
AYHLSKMGAHVVLTARSEEGLQKVVSRCLELGAASAHYIAGTMEDMTFAE
QFIVKAGKLMGGLDMLILNHITQTSLSLFHDDIHSVRRVMEVNFLSYVVM
STAALPMLKQSNGSIAVISSLAGKMT*Y*PMIAPYSASKFALDGFFSTIRTE
LYITKVNVSITLCVLGLIDTETAMKEISGIINAQASPKEECALEIIKGTA
LRKSEVYYDKSPLTPILLGNPGRKIMEFFSLRYYNKDMFVSN (SEQ ID NO:6)

FIG. 5

Single mutant; I231V nucleotide sequence
*Changes reflected by bold, italic, and enlarged font.

ATGGCAGTTATGAAAAATTACCTCCTCCCGATCCTGGTGCTCTTCCTGGCC
TACTACTACTATTCTACAAATGAAGAGTTCAGACCAGAAATGCTCCAGGG
AAAGAAAGTGATTGTCACTGGGGCCAGCAAAGGGATTGGAAGAGAAATG
GCATATCATCTGTCAAAAATGGGAGCCCATGTGGTATTGACTGCCAGGTC
GGAGGAAGGTCTCCAGAAGGTAGTGTCTCGCTGCCTTGAACTCGGAGCAG
CCTCTGCTCACTACATTGCTGGCACTATGGAAGACATGACATTTGCGGAGC
AATTTATTGTCAAGGCGGGAAAGCTCATGGGCGGACTGGACATGCTTATT
CTAAACCACATCACTCAGACCTCGCTGTCTCTCTTCCATGACGACATCCAC
TCTGTGCGAAGAGTCATGGAGGTCAACTTCCTCAGCTACGTGGTCATGAG
CACAGCCGCCTTGCCCATGCTGAAGCAGAGCAATGGCAGCATTGCCGTCA
TCTCCTCCTTGGCTGGGAAAATGACCTATCCTATGATTGCTCCCTACTCTG
CAAGCAAGTTTGCTCTGGATGGGTTCTTTTCCACCATTAGAACAGAACTCT
ACATAACCAAGGTCAACGTGTCCATCACTCTCTGTGTCCTTGGCCTCATAG
ACACAGAAACAGCTATGAAGGAAATCTCTGGGATA*GTT*AACATGCAAGC
TTCTCCCAAGGAGGAGTGCGCCCTGGAGATCATCAAAGGCACAGCTCTAC
GCAAAAGCGAGGTGTACTATGACAAATCGCCTTTGACTCCAATCCTGCTTG
GGAACCCAGGAAGGAAGATCATGGAATTTTTTTCATTACGATATTATAAT
AAGGACATGTTTGTAAGTAACTAG (SEQ ID NO:7)

Single mutant: I231V peptide sequence

MAVMKNYLLPILVLFLAYYYYSTNEEFRPEMLQGKKVIVTGASKGIGREM
AYHLSKMGAHVVLTARSEEGLQKVVSRCLELGAASAHYIAGTMEDMTFAE
QFIVKAGKLMGGLDMLILNHITQTSLSLFHDDIHSVRRVMEVNFLSYVVM
STAALPMLKQSNGSIAVISSLAGKMTQPMIAPYSASKFALDGFFSTIRTE
LYITKVNVSITLCVLGLIDTETAMKEISGI*V*NAQASPKEECALEIIKGTA
LRKSEVYYDKSPLTPILLGNPGRKIMEFFSLRYYNKDMFVSN (SEQ ID NO:8)

FIG. 6

Single mutant: A233M nucleic acid sequence
*Changes reflected by bold, italic, and enlarged font.

GTCTCCAGAAGGTAGTGTCTCGCTGCCTTGAACTCGGAGCAGCCTCTGCTC
ACTACATTGCTGGCACTATGGAAGACATGACATTTGCGGAGCAATTTATTG
TCAAGGCGGGAAAGCTCATGGGCGGACTGGACATGCTTATTCTAAACCAC
ATCACTCAGACCTCGCTGTCTCTCTTCCATGACGACATCCACTCTGTGCGA
AGAGTCATGGAGGTCAACTTCCTCAGCTACGTGGTCATGAGCACAGCCGC
CTTGCCCATGCTGAAGCAGAGCAATGGCAGCATTGCCGTCATCTCCTCCTT
GGCTGGGAAAATGACCTATCCTATGATTGCTCCCTACTCTGCAAGCAAGTT
TGCTCTGGATGGGTTCTTTTCCACCATTAGAACSAGAACTCTACATAACCAA
GGTCAACGTGTCCATCACTCTCTGTGTCCTTGGCCTCATAGACACAGAAAC
AGCTATGAAGGAAATCTCTGGGATAGTTAAC*ATG*CAAGCTTCTCCCAAG
GAGGAGTGCGCCCTGGAGATCATCAAAGGCACAGCTCTACGCAAAAGCG
AGGTGTACTATGACAAATCGCCTTTGACTCCAATCCTGCTTGGGAACCCAG
GAAGGAAGATCATGGAATTTTTTTCATTACGATATTATAATAAGGACATGT
TTGTAAGTAACTAG (SEQ ID NO:9)

Single mutant: A233M peptide sequence
MAVMKNYLLPILVLFLAYYYYSTNEEFRPEMLQGKKVIVTGASKGIGREM
AYHLSKMGAHVVLTARSEEGLQKVVSRCLELGAASAHYIAGTMEDMTFAE
QFIVKAGKLMGGLDMLILNHITQTSLSLFHDDIHSVRRVMEVNFLSYVVM
STAALPMLKQSNGSIAVISSLAGKMTQPMIAPYSASKFALDGFFSTIRTE
LYITKVNVSITLCVLGLIDTETAMKEISGIIN*M*QASPKEECALEIIKGTA
LRKSEVYYDKSPLTPILLGNPGRKIMEFFSLRYYNKDMFVSN (SEQ ID NO:10)

FIG. 7

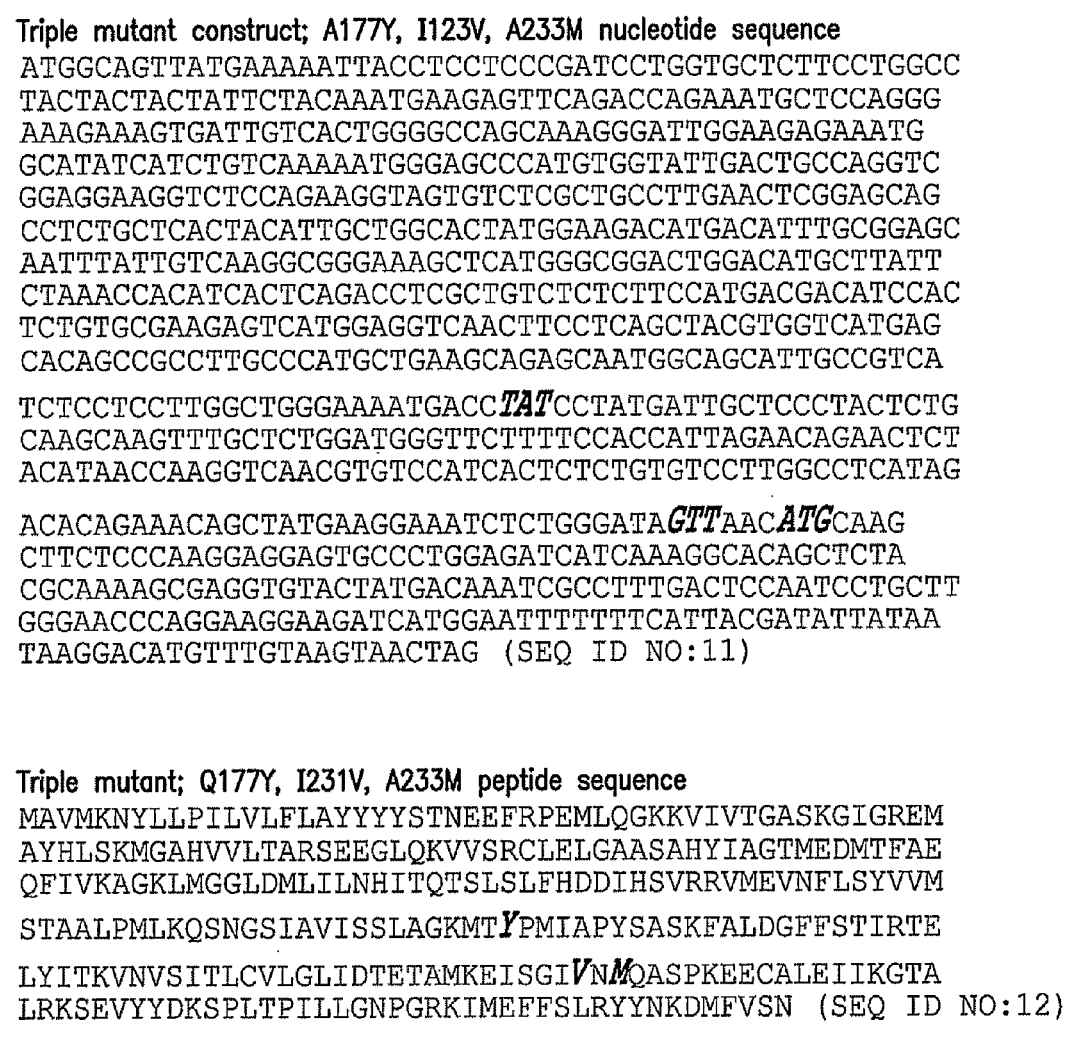

Triple mutant construct; A177Y, I123V, A233M nucleotide sequence

ATGGCAGTTATGAAAAATTACCTCCTCCCGATCCTGGTGCTCTTCCTGGCC
TACTACTACTATTCTACAAATGAAGAGTTCAGACCAGAAATGCTCCAGGG
AAAGAAAGTGATTGTCACTGGGGCCAGCAAAGGGATTGGAAGAGAAATG
GCATATCATCTGTCAAAAATGGGAGCCCATGTGGTATTGACTGCCAGGTC
GGAGGAAGGTCTCCAGAAGGTAGTGTCTCGCTGCCTTGAACTCGGAGCAG
CCTCTGCTCACTACATTGCTGGCACTATGGAAGACATGACATTTGCGGAGC
AATTTATTGTCAAGGCGGGAAAGCTCATGGGCGGACTGGACATGCTTATT
CTAAACCACATCACTCAGACCTCGCTGTCTCTCTTCCATGACGACATCCAC
TCTGTGCGAAGAGTCATGGAGGTCAACTTCCTCAGCTACGTGGTCATGAG
CACAGCCGCCTTGCCCATGCTGAAGCAGAGCAATGGCAGCATTGCCGTCA
TCTCCTCCTTGGCTGGGAAAATGACC*TAT*CCTATGATTGCTCCCTACTCTG
CAAGCAAGTTTGCTCTGGATGGGTTCTTTTCCACCATTAGAACAGAACTCT
ACATAACCAAGGTCAACGTGTCCATCACTCTCTGTGTCCTTGGCCTCATAG
ACACAGAAACAGCTATGAAGGAAATCTCTGGGATA*GTT*AAC*ATG*CAAG
CTTCTCCCAAGGAGGAGTGCCCTGGAGATCATCAAAGGCACAGCTCTA
CGCAAAAGCGAGGTGTACTATGACAAATCGCCTTTGACTCCAATCCTGCTT
GGGAACCCAGGAAGGAAGATCATGGAATTTTTTTCATTACGATATTATAA
TAAGGACATGTTTGTAAGTAACTAG (SEQ ID NO:11)

Triple mutant; Q177Y, I231V, A233M peptide sequence

MAVMKNYLLPILVLFLAYYYYSTNEEFRPEMLQGKKVIVTGASKGIGREM
AYHLSKMGAHVVLTARSEEGLQKVVSRCLELGAASAHYIAGTMEDMTFAE
QFIVKAGKLMGGLDMLILNHITQTSLSLFHDDIHSVRRVMEVNFLSYVVM
STAALPMLKQSNGSIAVISSLAGKMT*Y*PMIAPYSASKFALDGFFSTIRTE
LYITKVNVSITLCVLGLIDTETAMKEISGI*V*N*M*QASPKEECALEIIKGTA
LRKSEVYYDKSPLTPILLGNPGRKIMEFFSLRYYNKDMFVSN (SEQ ID NO:12)

FIG. 8

Hexamutant; Q177Y, I180V, E226A, I227V, I231V, A233M nucleotide sequence. Changes reflected by bold, italicized, and enlarged font.

ATGGCAGTTATGAAAAATTACCTCCTCCCGATCCTGGTGCTCTTCCTGGCC
TACTACTACTATTCTACAAATGAAGAGTTCAGACCAGAAATGCTCCAGGG
AAAGAAAGTGATTGTCACTGGGGCCAGCAAAGGGATTGGAAGAGAAATG
GCATATCATCTGTCAAAAATGGGAGCCCATGTGGTATTGACTGCCAGGTC
GGAGGAAGGTCTCCAGAAGGTAGTGTCTCGCTGCCTTGAACTCGGAGCAG
CCTCTGCTCACTACATTGCTGGCACTATGGAAGACATGACATTTGCGGAGC
AATTTATTGTCAAGGCGGGAAAGCTCATGGGCGGACTGGACATGCTTATT
CTAAACCACATCACTCAGACCTCGCTGTCTCTCTTCCATGACGACATCCAC
TCTGTGCGAAGAGTCATGGAGGTCAACTTCCTCAGCTACGTGGTCATGAG
CACAGCCGCCTTGCCCATGCTGAAGCAGAGCAATGGCAGCATTGCCGTCA

TCTCCTCCTTGGCTGGGAAAATGACC*TAT*CCTATG*ATT*GCTCCCTACTCT
GCAAGCAAGTTTGCTCTGGATGGGTTCTTTTCCACCATTAGAACAGAACTC
TACATAACCAAGGTCAACGTGTCCATCACTCTCTGTGTCCTTGGCCTCATA

GACACAGAAACAGCTATGAAG*GAAATC*TCTGGGATA*GTT*AAC*ATG*C
AAGCTTCTCCCAAGGAGGAGTGCCCTGGAGATCATCAAAGGCACAGCT
CTACGCAAAAGCGAGGTGTACTATGACAAATCGCCTTTGACTCCAATCCT
GCTTGGGAACCCAGGAAGGAAGATCATGGAATTTTTTTCATTACGATATTA
TAATAAGGACATGTTTGTAAGTAACTAG (SEQ ID NO:13)

Hexamutant; Q177Y, I180V, E226A, I227V, I231V, A233M peptide sequence
MAVMKNYLLPILVLFLAYYYSTNEEFRPEMLQGKKVIVTGASKGIGREM
AYHLSKMGAHVVLTARSEEGLQKVVSRCLELGAASAHYIAGTMEDMTFAE
QFIVKAGKLMGGLDMLILNHITQTSLSLFHDDIHSVRRVMEVNFLSYVVM
STAALPMLKQSNGSIAVISSLAGKMT*Y*PM*V*APYSASKFALDGFFSTIRTE
LYITKVNVSITLCVLGLIDTETAMK*A V*SGI*V*N*M*QASPKEECALEIIKGTA
LRKSEVYYDKSPLTPILLGNPGRKIMEFFSLRYYNKDMFVSN (SEQ ID NO:14)

FIG. 9

SEQUENCE LISTING

```
<160> NUMBER OF SEQ ID NOS: 20

<210> SEQ ID NO 1
<211> LENGTH: 879
<212> TYPE: DNA
<213> ORGANISM: Homo sapiens

<400> SEQUENCE: 1
atggctttta tgaaaaaata tctcctcccc attctggggc tcttcatggc ctactactac      60
tattctgcaa acgaggaatt cagaccagag atgctccaag gaaagaaagt gattgtcaca     120
ggggccagca aagggatcgg aagagagatg gcttatcatc tggcgaagat gggagcccat     180
gtggtggtga cagcgaggtc aaaagaaact ctacagaagg tggtatccca ctgcctggag     240
cttggagcag cctcagcaca ctacattgct ggcaccatgg aagacatgac cttcgcagag     300
caatttgttg cccaagcagg aaagctcatg ggaggactag acatgctcat tctcaaccac     360
atcaccaaca cttctttgaa tcttttttcat gatgatattc accatgtgcg caaaagcatg     420
gaagtcaact tcctcagtta cgtggtcctg actgtagctg ccttgcccat gctgaagcag     480
agcaatggaa gcattgttgt cgtctcctct ctggctggga aagtggctta tccaatggtt     540
gctgcctatt ctgcaagcaa gtttgctttg gatgggttct tctcctccat cagaaaggaa     600
tattcagtgt ccagggtcaa tgtatcaatc actctctgtg ttcttggcct catagacaca     660
gaaacagcca tgaaggcagt ttctgggata gtccatatgc aagcagctcc aaaggaggaa     720
tgtgccctgg agatcatcaa aggggagct ctgcgccaag aagaagtgta ttatgacagc     780
tcactctgga ccactcttct gatcagaaat ccatgcagga agatcctgga atttctctac     840
tcaacgagct ataatatgga cagattcata aacaagtag                            879

<210> SEQ ID NO 2
<211> LENGTH: 292
<212> TYPE: PRT
<213> ORGANISM: Homo sapiens

<400> SEQUENCE: 2
```

Met Ala Phe Met Lys Lys Tyr Leu Leu Pro Ile Leu Gly Leu Phe Met
1               5                   10                  15

Ala Tyr Tyr Tyr Ser Ala Asn Glu Glu Phe Arg Pro Glu Met Leu
            20                  25                  30

Gln Gly Lys Lys Val Ile Val Thr Gly Ala Ser Lys Gly Ile Gly Arg
            35                  40                  45

Glu Met Ala Tyr His Leu Ala Lys Met Gly Ala His Val Val Thr
50                  55                  60

Ala Arg Ser Lys Glu Thr Leu Gln Lys Val Val Ser His Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Val Ala Gln Ala Gly Lys Leu Met Gly Gly
                100                 105                 110

Leu Asp Met Leu Ile Leu Asn His Ile Thr Asn Thr Ser Leu Asn Leu
            115                 120                 125

Phe His Asp Asp Ile His His Val Arg Lys Ser Met Glu Val Asn Phe
            130                 135                 140

Leu Ser Tyr Val Val Leu Thr Val Ala Ala Leu Pro Met Leu Lys Gln
145                 150                 155                 160

Ser Asn Gly Ser Ile Val Val Ser Ser Leu Ala Gly Lys Val Ala
                165                 170                 175

Tyr Pro Met Val Ala Ala Tyr Ser Ala Ser Lys Phe Ala Leu Asp Gly
            180                 185                 190

Phe Phe Ser Ser Ile Arg Lys Glu Tyr Ser Val Ser Arg Val Asn Val
            195                 200                 205

Ser Ile Thr Leu Cys Val Leu Gly Leu Ile Asp Thr Glu Thr Ala Met
210                 215                 220

Lys Ala Val Ser Gly Ile Val His Met Gln Ala Ala Pro Lys Glu Glu
225                 230                 235                 240

Cys Ala Leu Glu Ile Ile Lys Gly Gly Ala Leu Arg Gln Glu Glu Val
                245                 250                 255

Tyr Tyr Asp Ser Ser Leu Trp Thr Thr Leu Leu Ile Arg Asn Pro Cys
                260                 265                 270

Arg Lys Ile Leu Glu Phe Leu Tyr Ser Thr Ser Tyr Asn Met Asp Arg
            275                 280                 285

Phe Ile Asn Lys
            290

<210> SEQ ID NO 3
<211> LENGTH: 879
<212> TYPE: DNA
<213> ORGANISM: Mus musculus

<400> SEQUENCE: 3
atggcagtta tgaaaaatta cctcctcccg atcctggtgc tcttcctggc ctactactac      60
tattctacaa atgaagagtt cagaccagaa atgctccagg gaaagaaagt gattgtcact     120
ggggccagca aagggattgg aagagaaatg gcatatcatc tgtcaaaaat gggagcccat     180
gtggtattga ctgccaggtc ggaggaaggt ctccagaagg tagtgtctcg ctgccttgaa     240
ctcggagcag cctctgctca ctacattgct ggcactatgg aagacatgac atttgcggag     300
caatttattg tcaaggcggg aaagctcatg ggcggactgg acatgcttat tctaaaccac     360
atcactcaga cctcgctgtc tctcttccat gacgacatcc actctgtgcg aagagtcatg     420
gaggtcaact tcctcagcta cgtggtcatg agcacagccg ccttgcccat gctgaagcag     480

```
agcaatggca gcattgccgt catctcctcc ttggctggga aaatgaccca gcctatgatt    540
gctccctact ctgcaagcaa gtttgctctg gatgggttct tttccaccat tagaacagaa    600
ctctacataa ccaaggtcaa cgtgtccatc actctctgtg tccttggcct catagacaca    660
gaaacagcta tgaaggaaat ctctgggata attaacgccc aagcttctcc caaggaggag    720
tgcgccctgg agatcatcaa aggcacagct acgcaaaa gcgaggtgta ctatgacaaa      780
tcgcctttga ctccaatcct gcttgggaac ccaggaagga gatcatgga atttttttca     840 ttacgatatt ataataagga catgtttgta agtaactag                           879
```

<210> SEQ ID NO 4
<211> LENGTH: 292
<212> TYPE: PRT
<213> ORGANISM: Mus musculus

<400> SEQUENCE: 4

```
Met Ala Val Met Lys Asn Tyr Leu Leu Pro Ile Leu Val Leu Phe Leu
1               5                   10                  15

Ala Tyr Tyr Tyr Ser Thr Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ser Lys Met Gly Ala His Val Val Leu Thr
    50                  55                  60

Ala Arg Ser Glu Glu Gly Leu Gln Lys Val Val Ser Arg Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
    130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Lys Met Thr
                165                 170                 175

Gln Pro Met Ile Ala Pro Tyr Ser Ala Ser Lys Phe Ala Leu Asp Gly
            180                 185                 190

Phe Phe Ser Thr Ile Arg Thr Glu Leu Tyr Ile Thr Lys Val Asn Val
        195                 200                 205

Ser Ile Thr Leu Cys Val Leu Gly Leu Ile Asp Thr Glu Thr Ala Met
    210                 215                 220

Lys Glu Ile Ser Gly Ile Ile Asn Ala Gln Ala Ser Pro Lys Glu Glu
225                 230                 235                 240

Cys Ala Leu Glu Ile Ile Lys Gly Thr Ala Leu Arg Lys Ser Glu Val
                245                 250                 255

Tyr Tyr Asp Lys Ser Pro Leu Thr Pro Ile Leu Leu Gly Asn Pro Gly
            260                 265                 270

Arg Lys Ile Met Glu Phe Phe Ser Leu Arg Tyr Tyr Asn Lys Asp Met
        275                 280                 285

Phe Val Ser Asn
    290
```

<210> SEQ ID NO 5
<211> LENGTH: 879
<212> TYPE: DNA
<213> ORGANISM: Mus musculus

<400> SEQUENCE: 5

```
atggcagtta tgaaaaatta cctcctcccg atcctggtgc tcttcctggc ctactactac      60
tattctacaa atgaagagtt cagaccagaa atgctccagg gaaagaaagt gattgtcact     120
ggggccagca aagggattgg aagagaaatg gcatatcatc tgtcaaaaat gggagcccat     180
gtggtattga ctgccaggtc ggaggaaggt ctccagaagg tagtgtctcg ctgccttgaa     240
ctcggagcag cctctgctca ctacattgct ggcactatgg aagacatgac atttgcggag     300
caatttattg tcaaggcggg aaagctcatg ggcggactgg acatgcttat tctaaaccac     360
atcactcaga cctcgctgtc tcttcttccat gacgacatcc actctgtgcg aagagtcatg     420
gaggtcaact cctcagcta cgtggtcatg agcacagccg ccttgcccat gctgaagcag     480
agcaatggca gcattgccgt catctcctcc ttggctggga aaatgaccta tcctatgatt     540
gctccctact ctgcaagcaa gtttgctctg gatgggttct tttccaccat tagaacagaa     600
ctctacataa ccaaggtcaa cgtgtccatc actctctgtg tccttggcct catagacaca     660
gaaacagcta tgaaggaaat ctctgggata attaacgccc aagcttctcc caaggaggag     720
tgcgccctgg agatcatcaa aggcacagct ctacgcaaaa gcgaggtgta ctatgacaaa     780
tcgcctttga ctccaatcct gcttgggaac ccaggaagga agatcatgga atttttttca     840
ttacgatatt ataataagga catgtttgta agtaactag                            879
```

<210> SEQ ID NO 6
<211> LENGTH: 292
<212> TYPE: PRT
<213> ORGANISM: Mus musculus

<400> SEQUENCE: 6

Met Ala Val Met Lys Asn Tyr Leu Leu Pro Ile Leu Val Leu Phe Leu
1               5                   10                  15

Ala Tyr Tyr Tyr Tyr Ser Thr Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ser Lys Met Gly Ala His Val Val Leu Thr
    50                  55                  60

Ala Arg Ser Glu Glu Gly Leu Gln Lys Val Val Ser Arg Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
    130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Lys Met Thr
                165                 170                 175

Tyr Pro Met Ile Ala Pro Tyr Ser Ala Ser Lys Phe Ala Leu Asp Gly

```
            180                 185                 190
Phe Phe Ser Thr Ile Arg Thr Glu Leu Tyr Ile Thr Lys Val Asn Val
        195                 200                 205

Ser Ile Thr Leu Cys Val Leu Gly Leu Ile Asp Thr Glu Thr Ala Met
        210                 215                 220

Lys Glu Ile Ser Gly Ile Ile Asn Ala Gln Ala Ser Pro Lys Glu Glu
225                 230                 235                 240

Cys Ala Leu Glu Ile Ile Lys Gly Thr Ala Leu Arg Lys Ser Glu Val
                245                 250                 255

Tyr Tyr Asp Lys Ser Pro Leu Thr Pro Ile Leu Leu Gly Asn Pro Gly
            260                 265                 270

Arg Lys Ile Met Glu Phe Phe Ser Leu Arg Tyr Tyr Asn Lys Asp Met
        275                 280                 285

Phe Val Ser Asn
        290

<210> SEQ ID NO 7
<211> LENGTH: 879
<212> TYPE: DNA
<213> ORGANISM: Mus musculus

<400> SEQUENCE: 7
atggcagtta tgaaaaatta cctcctcccg atcctggtgc tcttcctggc ctactactac     60
tattctacaa tgaagagtt cagaccagaa atgctccagg gaaagaaagt gattgtcact    120
ggggccagca agggattgg aagagaaatg gcatatcatc tgtcaaaaat gggagcccat    180
gtggtattga ctgccaggtc ggaggaaggt ctccagaagg tagtgtctcg ctgccttgaa    240
ctcggagcag cctctgctca ctacattgct ggcactatgg aagacatgac atttgcggag    300
caatttattg tcaaggcggg aaagctcatg ggcggactgg acatgcttat tctaaaccac    360
atcactcaga cctcgctgtc tctcttccat gacgacatcc actctgtgcg aagagtcatg    420
gaggtcaact tcctcagcta cgtggtcatg agcacagccg ccttgcccat gctgaagcag    480
agcaatggca gcattgccgt catctcctcc ttggctggga aaatgaccta tcctatgatt    540
gctccctact ctgcaagcaa gtttgctctg gatgggttct tttccaccat tagaacagaa    600
ctctacataa ccaaggtcaa cgtgtccatc actctctgtg tccttggcct catagacaca    660
gaaacagcta tgaaggaaat ctctgggata gttaacatgc aagcttctcc caaggaggag    720
tgcgccctgg agatcatcaa aggcacagct tacgcaaaa gcgaggtgta ctatgacaaa    780
tcgcctttga ctccaatcct gcttgggaac ccaggaagga gatcatgga attttttca    840 ttacgatatt ataataagga catgtttgta agtaactag                            879

<210> SEQ ID NO 8
<211> LENGTH: 292
<212> TYPE: PRT
<213> ORGANISM: Mus musculus

<400> SEQUENCE: 8

Met Ala Val Met Lys Asn Tyr Leu Leu Pro Ile Leu Val Leu Phe Leu
1               5                   10                  15

Ala Tyr Tyr Tyr Ser Thr Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ser Lys Met Gly Ala His Val Val Leu Thr
    50                  55                  60
```

```
Ala Arg Ser Glu Glu Gly Leu Gln Lys Val Val Ser Arg Cys Leu Glu
 65                  70                  75                  80

Leu Gly Ala Ala Ser Ala His Tyr Ile Ala Gly Thr Met Glu Asp Met
             85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
    130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Lys Met Thr
                165                 170                 175

Gln Pro Met Ile Ala Pro Tyr Ser Ala Ser Lys Phe Ala Leu Asp Gly
            180                 185                 190

Phe Phe Ser Thr Ile Arg Thr Glu Leu Tyr Ile Thr Lys Val Asn Val
    195                 200                 205

Ser Ile Thr Leu Cys Val Leu Gly Leu Ile Asp Thr Glu Thr Ala Met
210                 215                 220

Lys Glu Ile Ser Gly Ile Val Asn Ala Gln Ala Ser Pro Lys Glu Glu
225                 230                 235                 240

Cys Ala Leu Glu Ile Ile Lys Gly Thr Ala Leu Arg Lys Ser Glu Val
                245                 250                 255

Tyr Tyr Asp Lys Ser Pro Leu Thr Pro Ile Leu Leu Gly Asn Pro Gly
            260                 265                 270

Arg Lys Ile Met Glu Phe Phe Ser Leu Arg Tyr Tyr Asn Lys Asp Met
    275                 280                 285

Phe Val Ser Asn
    290
```

<210> SEQ ID NO 9
<211> LENGTH: 671
<212> TYPE: DNA
<213> ORGANISM: Mus musculus

<400> SEQUENCE: 9

```
gtctccagaa ggtagtgtct cgctgccttg aactcggagc agcctctgct cactacattg    60
ctggcactat ggaagacatg acatttgcgg agcaatttat tgtcaaggcg ggaaagctca   120
tgggcggact ggacatgctt attctaaacc acatcactca gacctcgctg tctctcttcc   180
atgacgacat ccactctgtg cgaagagtca tggaggtcaa cttcctcagc tacgtggtca   240
tgagcacagc cgccttgccc atgctgaagc agagcaatgg cagcattgcc gtcatctcct   300
ccttggctgg aaaatgacc tatcctatga ttgctcccta ctctgcaagc aagtttgctc   360
tggatgggtt cttttccacc attagaacag aactctacat aaccaaggtc aacgtgtcca   420
tcactctctg tgtccttggc ctcatagaca cagaaacagc tatgaaggaa atctctggga   480
tagttaacat gcaagcttct cccaaggagg agtgcgccct ggagatcatc aaaggcacag   540
ctctacgcaa aagcgaggtg tactatgaca aatcgccttt gactccaatc ctgcttggga   600
acccaggaag gaagatcatg gaattttttt cattacgata ttataataag gacatgtttg   660
taagtaacta g                                                        671
```

<210> SEQ ID NO 10

```
<211> LENGTH: 292
<212> TYPE: PRT
<213> ORGANISM: Mus musculus

<400> SEQUENCE: 10

Met Ala Val Met Lys Asn Tyr Leu Leu Pro Ile Leu Val Leu Phe Leu
1               5                   10                  15

Ala Tyr Tyr Tyr Ser Thr Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ser Lys Met Gly Ala His Val Val Leu Thr
50                  55                  60

Ala Arg Ser Glu Glu Gly Leu Gln Lys Val Val Ser Arg Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Lys Met Thr
                165                 170                 175

Gln Pro Met Ile Ala Pro Tyr Ser Ala Ser Lys Phe Ala Leu Asp Gly
            180                 185                 190

Phe Phe Ser Thr Ile Arg Thr Glu Leu Tyr Ile Thr Lys Val Asn Val
        195                 200                 205

Ser Ile Thr Leu Cys Val Leu Gly Leu Ile Asp Thr Glu Thr Ala Met
210                 215                 220

Lys Glu Ile Ser Gly Ile Ile Asn Met Gln Ala Ser Pro Lys Glu Glu
225                 230                 235                 240

Cys Ala Leu Glu Ile Ile Lys Gly Thr Ala Leu Arg Lys Ser Glu Val
                245                 250                 255

Tyr Tyr Asp Lys Ser Pro Leu Thr Pro Ile Leu Leu Gly Asn Pro Gly
            260                 265                 270

Arg Lys Ile Met Glu Phe Phe Ser Leu Arg Tyr Tyr Asn Lys Asp Met
        275                 280                 285

Phe Val Ser Asn
    290

<210> SEQ ID NO 11
<211> LENGTH: 879
<212> TYPE: DNA
<213> ORGANISM: Mus musculus

<400> SEQUENCE: 11
atggcagtta tgaaaaatta cctcctcccg atcctggtgc tcttcctggc ctactactac     60
tattctacaa atgaagagtt cagaccagaa atgctccagg gaaagaaagt gattgtcact    120
ggggccagca aagggattgg aagagaaatg gcatatcatc tgtcaaaaat gggagcccat    180
gtggtattga ctgccaggtc ggaggaaggt ctccagaagg tagtgtctcg ctgccttgaa    240
ctcggagcag cctctgctca ctacattgct ggcactatgg aagacatgac atttgcggag    300
```

```
caatttattg tcaaggcggg aaagctcatg gcggactgg acatgcttat tctaaaccac    360
atcactcaga cctcgctgtc tctcttccat gacgacatcc actctgtgcg aagagtcatg    420
gaggtcaact tcctcagcta cgtggtcatg agcacagccg ccttgcccat gctgaagcag    480
agcaatggca gcattgccgt catctcctcc ttggctggga aaatgaccta tcctatgatt    540
gctccctact ctgcaagcaa gtttgctctg gatgggttct tttccaccat tagaacagaa    600
ctctacataa ccaaggtcaa cgtgtccatc actctctgtg tccttggcct catagacaca    660
gaaacagcta tgaaggaaat ctctgggata gttaacatgc aagcttctcc caaggaggag    720
tgcgccctgg agatcatcaa aggcacagct ctacgcaaaa gcgaggtgta ctatgacaaa    780
tcgcctttga ctccaatcct gcttgggaac ccaggaagga agatcatgga attttttca    840 ttacgatatt ataataagga catgtttgta agtaactag                            879
```

<210> SEQ ID NO 12
<211> LENGTH: 292
<212> TYPE: PRT
<213> ORGANISM: Mus musculus

<400> SEQUENCE: 12

```
Met Ala Val Met Lys Asn Tyr Leu Leu Pro Ile Leu Val Leu Phe Leu
1               5                   10                  15

Ala Tyr Tyr Tyr Tyr Ser Thr Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ser Lys Met Gly Ala His Val Val Leu Thr
    50                  55                  60

Ala Arg Ser Glu Glu Gly Leu Gln Lys Val Val Ser Arg Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
    130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Lys Met Thr
                165                 170                 175

Tyr Pro Met Ile Ala Pro Tyr Ser Ala Ser Lys Phe Ala Leu Asp Gly
            180                 185                 190

Phe Phe Ser Thr Ile Arg Thr Glu Leu Tyr Ile Thr Lys Val Asn Val
        195                 200                 205

Ser Ile Thr Leu Cys Val Leu Gly Leu Ile Asp Thr Glu Thr Ala Met
    210                 215                 220

Lys Glu Ile Ser Gly Ile Val Asn Met Gln Ala Ser Pro Lys Glu Glu
225                 230                 235                 240

Cys Ala Leu Glu Ile Ile Lys Gly Thr Ala Leu Arg Lys Ser Glu Val
                245                 250                 255

Tyr Tyr Asp Lys Ser Pro Leu Thr Pro Ile Leu Leu Gly Asn Pro Gly
            260                 265                 270
```

```
Arg Lys Ile Met Glu Phe Phe Ser Leu Arg Tyr Tyr Asn Lys Asp Met
        275                 280                 285

Phe Val Ser Asn
    290
```

<210> SEQ ID NO 13
<211> LENGTH: 879
<212> TYPE: DNA
<213> ORGANISM: Mus musculus

<400> SEQUENCE: 13

```
atggcagtta tgaaaaatta cctcctcccg atcctggtgc tcttcctggc ctactactac    60
tattctacaa atgaagagtt cagaccagaa atgctccagg gaaagaaagt gattgtcact   120
ggggccagca aagggattgg aagagaaatg gcatatcatc tgtcaaaaat gggagcccat   180
gtggtattga ctgccaggtc ggaggaaggt ctccagaagg tagtgtctcg ctgccttgaa   240
ctcggagcag cctctgctca ctacattgct ggcactatgg aagacatgac atttgcggag   300
caatttattg tcaaggcggg aaagctcatg ggcggactgg acatgcttat ctaaaccac    360
atcactcaga cctcgctgtc tctcttccat gacgacatcc actctgtgcg aagagtcatg   420
gaggtcaact tcctcagcta cgtggtcatg agcacagccg ccttgcccat gctgaagcag   480
agcaatggca gcattgccgt catctcctcc ttggctggga aaatgaccta tcctatgatt   540
gctccctact ctgcaagcaa gtttgctctg gatgggttct tttccaccat agaacagaa    600
ctctacataa ccaaggtcaa cgtgtccatc actctctgtg tccttggcct catagacaca   660
gaaacagcta tgaaggaaat ctctgggata gttaacatgc aagcttctcc caaggaggag   720
tgcgccctgg agatcatcaa aggcacagct ctacgcaaaa gcgaggtgta ctatgacaaa   780
tcgcctttga ctccaatcct gcttgggaac ccaggaagga gatcatgga  attttttca    840
ttacgatatt ataataagga catgtttgta agtaactag                           879
```

<210> SEQ ID NO 14
<211> LENGTH: 292
<212> TYPE: PRT
<213> ORGANISM: Mus musculus

<400> SEQUENCE: 14

```
Met Ala Val Met Lys Asn Tyr Leu Leu Pro Ile Leu Val Leu Phe Leu
1               5                   10                  15

Ala Tyr Tyr Tyr Ser Thr Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ser Lys Met Gly Ala His Val Val Leu Thr
    50                  55                  60

Ala Arg Ser Glu Glu Gly Leu Gln Lys Val Val Ser Arg Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
    130                 135                 140

Leu Ser Tyr Val Val Met Ser Thr Ala Ala Leu Pro Met Leu Lys Gln
```

```
             145                 150                 155                 160
Ser Asn Gly Ser Ile Ala Val Ile Ser Ser Leu Ala Gly Lys Met Thr
                165                 170                 175

Tyr Pro Met Val Ala Pro Tyr Ser Ala Ser Lys Phe Ala Leu Asp Gly
            180                 185                 190

Phe Phe Ser Thr Ile Arg Thr Glu Leu Tyr Ile Thr Lys Val Asn Val
        195                 200                 205

Ser Ile Thr Leu Cys Val Leu Gly Leu Ile Asp Thr Glu Thr Ala Met
    210                 215                 220

Lys Ala Val Ser Gly Ile Val Asn Met Gln Ala Ser Pro Lys Glu Glu
225                 230                 235                 240

Cys Ala Leu Glu Ile Ile Lys Gly Thr Ala Leu Arg Lys Ser Glu Val
                245                 250                 255

Tyr Tyr Asp Lys Ser Pro Leu Thr Pro Ile Leu Leu Gly Asn Pro Gly
            260                 265                 270

Arg Lys Ile Met Glu Phe Phe Ser Leu Arg Tyr Tyr Asn Lys Asp Met
        275                 280                 285

Phe Val Ser Asn
    290

<210> SEQ ID NO 15
<211> LENGTH: 23
<212> TYPE: DNA
<213> ORGANISM: Mus musculus

<400> SEQUENCE: 15
caccatggca gttatgaaaa att                                               23

<210> SEQ ID NO 16
<211> LENGTH: 24
<212> TYPE: DNA
<213> ORGANISM: Mus musculus

<400> SEQUENCE: 16
ctagttactt acaaacatgt cctt                                              24

<210> SEQ ID NO 17
<211> LENGTH: 34
<212> TYPE: DNA
<213> ORGANISM: Mus musculus

<400> SEQUENCE: 17
ggctgggaaa atgacctatc ctatgattgc tccc                                   34

<210> SEQ ID NO 18
<211> LENGTH: 47
<212> TYPE: DNA
<213> ORGANISM: Mus musculus

<400> SEQUENCE: 18
cagctatgaa ggaaatctct gggatagtta acatgcaagc ttctccc                     47

<210> SEQ ID NO 19
<211> LENGTH: 47
<212> TYPE: DNA
<213> ORGANISM: Mus musculus

<400> SEQUENCE: 19
cagctatgaa ggaaatctct gggatagtta acatgcaagc ttctccc                     47
```

```
<210> SEQ ID NO 20
<211> LENGTH: 48
<212> TYPE: DNA
<213> ORGANISM: Mus musculus

<400> SEQUENCE: 20
tcagtcgtca tcgtccttgt agtccatgtt acttacaaac atgtcctt          48
```

11β HYDROXYSTEROID DEHYDROGENASE TYPE 1

CROSS-REFERENCE TO RELATED APPLICATIONS

The present application is a 371 application of PCT/US2008/079132, filed Oct. 8, 2008, which claims priority benefit of U.S. provisional application Ser. No. 60/978,231, filed Oct. 8, 2007, each of which are incorporated by reference herein.

FIELD

The subject matter disclosed and claimed herein relates to mutant 11β-Hydroxysteroid Dehydrogenase type 1 ("11βHSD1") nucleic and amino acid sequences, expression of such sequences in cell-based assay systems, expression of mutant 11βHSD1 sequences in mice via homologous recombination, and assays for identifying and determining the effects of compounds on 11βHSD activity using the mutant 11βHSD1 sequences.

BACKGROUND

Recent evidence suggests that tissue concentrations of glucocorticoids, such as cortisol, can be controlled independently of circulating glucocorticoid concentrations. Walker et al., *Ann. N.Y. Acad. Sci.* 1083:165-184 (2006). This control may be attributed to local intracellular expression of 11βHSD1. 11βHSD1 is a microsomal enzyme that catalyzes the conversion of cortisone to cortisol. Cortisol has a wide range of physiological effects including; regulation of carbohydrate, protein and lipid metabolism, regulation of normal growth and development, influence on cognitive function, resistance to stress and mineralocorticoid activity. Cortisol stimulates hepatic gluconeogenesis and inhibits peripheral glucose uptake, the net effect of which is an increase in blood glucose concentration. Glucocorticoids are also essential in the regulation of the immune response. When circulating at higher concentrations, glucocorticoids are immunosuppressive and are used pharmacologically as anti-inflammatory agents.

There are two isoforms of 11βHSD: 11βHSD1 and 11βHSD2. Recent evidence suggests that disregulation of 11βHSD1 may lead to conditions typically associated with the metabolic syndrome, whereas the absence of 11βHSD2 is often associated with hypertension (Walker et al., supra.).

11βHSD1 is highly expressed in liver. It is also expressed at lower, buy physiologically relevant levels in adipose tissue, lung, and areas of the central nervous system. The primary in vivo function of 11βHSD1 is to convert cortisone to cortisol. (Walker et al., supra) As such, the literature suggests that the physiological role of 11βHSD1 is to maintain activation of the glucocorticoid receptor where required for proper metabolic activity. This may be particularly relevant during the trough phase of the diurnal rhythm of adrenal cortisol production. In cases where 11βHSD1 expression is inappropriately elevated, the increased cortisol levels in adipose tissue and liver would promote development of symptoms associated with metabolic diseases such as obesity, hyperglycemia, hyperlipidemia and hypertension. Inhibition of 11βHSD1 under these circumstances may provide a means to reduce cortisol levels and, as a result, abolish conditions associated with the metabolic disease. Thus, identification of compounds that modulate 11βHSD1 activity would be useful for developing treatments for diseases such as diabetes and obesity.

One of the challenges faced by those discovering and developing inhibitors of 11βHSD1 for clinical use is species specificity. It is often the case that inhibitors that are potent versus the human enzyme are significantly less potent against the enzyme in commonly used animal models. This significantly hampers the use of these animal models to judge the in vivo potency and efficacy of lead molecules, thereby making predictions of doses in clinical trials extremely difficult. For example, despite the approximately 80% homology at the amino acid level between human and mouse 11βHSD1, compounds that are very potent inhibitors of human 11βHSD1 are often found to be weakly potent inhibitors of mouse 11βHSD1. For instance, a bicyclic triazolopyridyl (TZP) compound designated "Compound A" has an $IC_{50}$ of 4 nM for human 11βHSD1. Yet the $IC_{50}$ for Compound A is 625 nM against mouse 11βHSD1—a 160 fold difference. This low potency versus the mouse enzyme would, for all practical purposes, preclude testing in mice.

Since most animal models of metabolic disease are murine based, the efficacy of a compound with a desirable in vitro potency profile versus the human enzyme cannot be confirmed in vivo prior to initiation of clinical trials. This leads to three potential issues for a drug discovery and developmental organization. First, compounds sometimes possess unanticipated benefits that can only be observed upon in vivo efficacy testing. Without an appropriate in vivo test, an otherwise desirable profile may be unintentionally discarded. Second, compounds that seem potent against the human enzyme in vitro may not perform well in vivo for unanticipated reasons. This leaves open the possibility that an undesirable compound may be progressed unnecessarily. Third, it severely confounds the estimation of efficacious human doses for clinical study. Thus, there remains a need for a reliable 11βHSD1 mouse model for screening compounds which modulate 11βHSD1 activity.

SUMMARY

In view of the above-referenced need(s), disclosed and claimed herein are both nucleic acid and polypeptide compositions comprising a mutant 11βHSD1 sequence that may be used to facilitate development of in vivo models. Further disclosed are the mutant 11βHSD1 sequences used to create the above-described animal models, and vectors and cells comprising the same. Additionally, the animal models may be used to perform methods to identify and/or characterize compounds that modulate 11βHSD1 activity. Further described is a genetically modified animal model expressing a mutant form of 11βHSD1 wherein the mutations confer a human-like phenotype, thereby making the animal a useful predictor of efficacious doses for humans. Preferably the model is a mouse model, however, the techniques and methods for creating the mouse model exemplified herein could readily be applied to other mammalian species including rat, monkey, chimpanzee, guinea pig, hamster, as well as other organisms such as *Xenopus*.

One aspect provides an isolated nucleic acid molecule encoding a polypeptide comprising at least one of SEQ ID NOs: 2, 4, 6, 8, 10 or 12, wherein the polypeptide has 11βHSD1 activity.

Another aspect provides an isolated nucleic acid molecule comprising a nucleotide sequence derived from a mouse 11βHSD1 gene, which encodes a modified amino acid sequence comprising a glutamine to tyrosine substitution at a position equivalent to amino acid 177 of the 11βHSD1 polypeptide, an isoleucine to valine at a position equivalent to amino acid 231 of the 11βHSD1 polypeptide and an alanine to methionine substitution at a position equivalent to amino acid 233 of the 11βHSD1 polypeptide, and wherein the modified amino acid sequence has 11βHSD1 activity.

Further disclosed is an isolated nucleic acid molecule comprising a nucleotide sequence derived from a mouse 11βHSD1 gene, which encodes a modified amino acid sequence comprising a glutamine to tyrosine substitution at a position equivalent to amino acid 177 of the 11βHSD1 polypeptide, wherein the modified amino acid sequence has 11βHSD1 activity.

In one embodiment, the isolated nucleic acid further comprises an isoleucine to valine substitution at a position equivalent to amino acid 231 of the 11βHSD1 polypeptide. In another embodiment, the isolated nucleic acid further comprises an alanine to methionine substitution at a position equivalent to amino acid 233 of the 11βHSD1 polypeptide.

Additional embodiments include: recombinant vectors comprising the nucleic acids described herein; recombinant host cells comprising such vectors; and isolated polypeptides comprising at least one of SEQ ID NOs: 2, 4, 6, 8, 10 or 12 wherein the polypeptides have 11βHSD1 activity.

Further described are isolated polypeptides comprising an amino acid sequence derived from a mouse 11βHSD1 polypeptide comprising a glutamine to tyrosine substitution at a position equivalent to amino acid 177 of the 11βHSD1 polypeptide, an isoleucine to valine at a position equivalent to amino acid 231 of the 11βHSD1 polypeptide and an alanine to methionine substitution at a position equivalent to amino acid 233 of the 11βHSD1 polypeptide.

An additional embodiment is an isolated polypeptide comprising an amino acid sequence derived from a mouse 11βHSD1 polypeptide comprising a glutamine to tyrosine substitution at a position equivalent to amino acid 177 of the 11βHSD1 polypeptide wherein the modified amino acid sequence has 11βHSD1 activity. In one embodiment, the isolated polypeptide further comprises an isoleucine to valine substitution at a position equivalent to amino acid 231 of the 11βHSD1 polypeptide. In another embodiment, the isolated polypeptide comprises an alanine to methionine substitution at a position equivalent to amino acid 233 of the 11βHSD1 polypeptide.

Another embodiment is a gene-targeted, non-human mammal (e.g., mouse, rat, monkey, or chimp) having a genome comprising a heterologous nucleic acid sequence encoding a modified 11βHSD1 polypeptide, wherein the heterologous nucleic acid sequence is under transcriptional control of endogenous regulatory sequences. In one embodiment, the gene-targeted, non-human animal is homozygous for the modified 11βHSD1 allele.

A further embodiment is an isolated, gene-targeted cell comprising a modified 11βHSD1 endogenous allele, wherein the modified 11βHSD1 endogenous allele is under transcriptional control of endogenous regulatory sequences, and wherein the modified 11βHSD1 allele encodes a polypeptide comprising at least one of SEQ ID NOs:2, 4, 6, 8, 10 or 12 and has 11βHSD1 activity.

Further described is an isolated, gene-targeted cell comprising a modified 11βHSD1 endogenous allele, wherein the modified 11βHSD1 endogenous allele is under transcriptional control of endogenous regulatory sequences, and wherein the modified 11βHSD1 allele encoding a modified amino acid sequence comprising a glutamine to tyrosine substitution at a position equivalent to amino acid 177 of the 11βHSD1 polypeptide and has 11βHSD1 activity.

Similarly, further described is an isolated, gene-targeted cell further comprises an isoleucine to valine substitution at a position equivalent to amino acid 231 of the 11βHSD1 polypeptide. In another embodiment, the isolated, gene-targeted cell further comprises an alanine to methionine substitution at a position equivalent to amino acid 233 of the 11βHSD1 polypeptide. In another embodiment, the isolated, gene-targeted cell is a mouse cell. In another embodiment, the mouse cell is a liver cell.

Finally, other embodiments include methods of identifying agents that inhibit 11βHSD1 activity, the methods comprising (a) preparing microsomes (e.g., liver) from a gene-targeted, non-human animal or from a gene-targeted cell; (b) contacting the microsomes with a test agent; and (c) measuring inhibition of 11βHSD1 activity. In one embodiment, the inhibition is determined by measuring cortisol concentration before and after contact with the test agent.

DESCRIPTION OF FIGURES

FIG. 1 depicts a diagram of the mutant 11βHSD1 targeting constructs.

FIG. 3 represents the nucleic acid sequence (SEQ ID NO:1) and amino acid sequence (SEQ ID NO:2) of wild-type human 11βHSD1.

FIG. 4 represents the nucleic acid sequence (SEQ ID NO:3) and amino acid sequence (SEQ ID NO:4) of wild-type mouse 11βHSD1.

FIG. 5 represents the nucleic acid sequence (SEQ ID NO:5) and amino acid sequence (SEQ ID NO:6) of the single mutant 11βHSD1 construct comprising the Q177Y mutation.

FIG. 6 represents the nucleic acid sequence (SEQ ID NO:7) and amino acid sequence (SEQ ID NO:8) of the single mutant 11βHSD1 construct comprising the I231Y mutation.

FIG. 7 represents the nucleic acid sequence (SEQ ID NO:9) and amino acid sequence (SEQ ID NO:10) of single mutant 11βHSD1 construct comprising the A233M mutation.

FIG. 8 represents the nucleic acid sequence (SEQ ID NO:11) and amino acid sequence (SEQ ID NO:12) of the mouse triple mutant 11βHSD1 construct comprising the Q177Y, I231Y and A233M mutations.

FIG. 9 represents the nucleic acid sequence (SEQ ID NO:13) and amino acid sequence (SEQ ID NO:14) of the hexamutant 11βHSD1 construct comprising Q177Y, I180V, E226A, I227V, I231V and A233M mutations.

DETAILED DESCRIPTION

Figure 2:
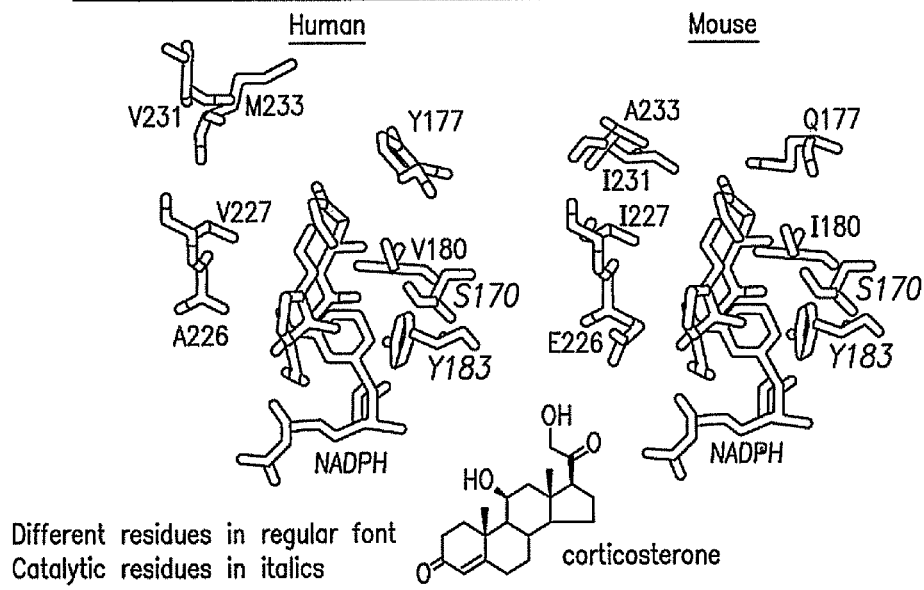
FIG. 2 shows models of the active sites for human and mouse 11βHSD1.

As used herein and in the appended claims, the singular forms "a", "and", and "the" include plural referents unless the context clearly dictates otherwise. Thus, for example, reference to "a non-human gene-targeted animal" includes a plurality of such animals and reference to "the 11βHSD1 gene" includes reference to one or more 11βHSD1 genes and equivalents thereof known to those skilled in the art, and so forth.

The definitions provided below are meant to guide those skilled in the art in interpreting the subject matter disclosed and claimed herein. The definitions control should a claim term or other term used in the specification be deemed unclear or ambiguous. Should a term not be expressly defined herein, the 2007 edition of Webster's dictionary should be consulted.

DEFINITIONS

As used herein, 11βHSD means 11 beta hydroxysteroid dehydrogenase. The definition includes 11βHSD from all species including: human, mouse, rat, guinea pig, and chimpanzee.

As used herein, 11βHSD1 refers to the type 1 isoform of 11βHSD. 11βHSD1 is implicated in regulating metabolic functions and plays a role in metabolic disease. This isoform functions predominantly as a reductase in vivo. In one embodiment, the wild-type human 11βHSD1 nucleic acid sequence comprises SEQ ID NO:1. In another embodiment, the wild-type human 11βHSD1 amino acid sequence comprises SEQ ID NO:2. In another embodiment, the wild-type mouse 11βHSD1 nucleic acid sequence comprises SEQ ID NO:3. In another embodiment, the wild-type mouse 11βHSD1 amino acid sequence comprises SEQ ID NO:4.

As used herein, 11βHSD2 refers to the type 2 isoform of 11βHSD. 11βHSD2 functions predominantly as a dehydrogenase in vivo and is implicated in salt regulation and hypertension.

As used herein, humanized means modification of a non-human nucleic or amino acid sequence to be similar to that of a human sequence.

As used herein, amino acids are represented by the full name thereof, by the three letter code corresponding thereto, or by the one-letter code corresponding thereto, as indicated below:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, a "functional" biological molecule is a biological molecule in a form in which it exhibits a property by which it is characterized. A functional enzyme, for example, is one which exhibits the catalytic activity by which the enzyme is characterized.

As used herein, the term "gene-targeted animal" refers to an animal whose genome comprises an exogenous polynucleotide which has been integrated into the animal's genome by homologous recombination. In one embodiment, the gene-targeted animal is a mouse expressing mutant 11βHSD1.

Hybridization reactions can be performed under conditions of different "stringency". Conditions that increase stringency of a hybridization reaction are widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

As used herein, "$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$, may be predicted according to a standard formula, such as: $T_m=81.5+16.6 \log [X^+]+0.41$ (% G/C)$-0.61$ (% F)$-600/L$ where $[X^+]$ is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

As used herein, the term "host cell" includes an individual cell or cell culture which can be or has been a recipient of any recombinant vector(s) or isolated polynucleotide described herein. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide described herein. A host cell which comprises a recombinant vector is a "recombinant host cell."

As used herein, "inhibitor" refers to an agent that reduces the biological activity of a target, such as 11βHSD. Inhibitors include small molecules, peptides, antibodies or fragments thereof (e.g., Fab fragments, single chain antibodies, domain antibodies), non-antibody binding proteins, antisense molecules and/or siRNA molecules.

As used herein, "inhibition" refers to reduction of the biological activity of a target, such as 11βHSD.

As used herein, the term "ligand" refers to a compound that specifically binds to a target receptor or enzyme.

As used herein, the term "modulate" refers to a change in activity of 11βHSD, for example by increasing or decreasing its activity.

As used herein, the term "modulator compound" refers to a compound or agent which effects the activity of 11βHSD either directly or indirectly. In one embodiment, a modulator compound inhibits 11βHSD thereby decreasing its activity.

As used herein, "mutant" means non-native. A typical convention for naming amino mutations is as follows: Q177Y would mean the "Q" or glutamine, at position 177 is changed to "Y" or tyrosine. Therefore the native amino acid is listed first (Q in the preceding example) the position of the amino acid in the peptide of interest (position 177), ending with the substituted amino acid (Y).

As used herein, "mutant 11βHSD1," "recombinant mutant 11βHSD1" or "modified 11βHSD1" refers to a nucleic acid sequence which encodes, or polypeptide sequence which comprises, at least one of the following mutations: glutamine to tyrosine substitution at a position equivalent to amino acid 177 of the 11βHSD1 polypeptide, an isoleucine to valine at a position equivalent to amino acid 231 of the 11βHSD1 polypeptide and an alanine to methionine substitution at a position equivalent to amino acid 233 of the 11βHSD1 polypeptide. In one embodiment, the "mutant 11βHSD1," "recombinant mutant 11βHSD1" or "modified 11βHSD1" comprises all three mutations of glutamine to tyrosine substitution at a position equivalent to amino acid 177 of the 11βHSD1 polypeptide, an isoleucine to valine at a position equivalent to amino acid 231 of the 11βHSD1 polypeptide and an alanine to methionine substitution at a position equivalent to amino acid 233 of the 11βHSD1 polypeptide. In another embodiment, the "mutant 11βHSD1," "recombinant mutant 11βHSD1" or "modified 11βHSD1" comprises six amino acid mutations of glutamine to tyrosine substitution at a position equivalent to amino acid 177 of the 11βHSD1 polypeptide, an isoleucine to valine at a position equivalent to amino acid 231 of the 11βHSD1 polypeptide, an alanine to methionine substitution at a position equivalent to amino acid 233, an isoleucine to valine at a position equivalent to amino acid 180, a glutamine to alanine at a position equivalent to amino acid 226, and an isoleucine to valine at a position equivalent to amino acid 227 of the 11βHSD1 polypeptide As used herein, "overexpression" refers to an expression level of a nucleic acid that is above the level typically expressed in a given cell or tissue type.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at http://ww.ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the term "probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, the term "receptor" refers to an agent that specifically binds to a ligand.

As used herein, the term "recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well. A host cell that comprises a recombinant polynucleotide is referred to as a "recombinant host cell." A gene which is expressed in a recombinant host cell wherein the gene comprises a recombinant polynucleotide, produces a "recombinant polypeptide."

As used herein, a "recombinant polypeptide" is one which is produced upon expression of a recombinant polynucleotide.

As used herein, the term "restriction endonuclease" refers to a restriction site that is a portion of a double-stranded nucleic acid which is recognized by a restriction endonuclease. A portion of a double-stranded nucleic acid is "recognized" by a restriction endonuclease if the endonuclease is capable of cleaving both strands of the nucleic acid at the portion when the nucleic acid and the endonuclease are contacted.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

As used herein, a "sequencing primer" is an oligonucleotide primer which is complementary to at least a portion of a polynucleotide and which can be elongated by a DNA or RNA polymerizing enzyme such as DNA polymerase, whereby binding of the sequencing primer to the polynucleotide and elongation of the primer using methods well known in the art yields an oligonucleotide transcript which is complementary to at least a part of the polynucleotide.

As used herein, the term "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. A "substantially pure nucleic acid" also refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, e.g., arresting its development; and (c) relieving the disease, e.g., causing regression of the disease.

The terms "individual," "subject," and "patient," used interchangeably herein, refer to a mammal, including, but not limited to, murines, simians, humans, canines and bovines.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, the term "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

It is to be understood that the subject matter disclosed and claimed herein is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art. Although any methods and materials similar or equivalent to those described herein can be used in the practice or testing of the subject matter described herein, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the subject matter described and claimed herein is not entitled to antedate such publication by virtue of prior invention. Further, the dates of publication provided may be different from the actual publication dates which may need to be independently confirmed.

General Approach

In order to improve the potencies of inhibitors of human 11β-Hydroxysteroid Dehydrogenase 1 ("11βHSD1") against the mouse enzyme, three dimensional models of the active sites of the two enzymes were constructed from the published high resolution crystal structures. A structural overlay of these models identified the corresponding amino acid resides within 5 Å of the substrate (see FIG. 2). Computational analysis of the binding of various inhibitor molecules suggested that three sets of mutations within the mouse sequence should be considered: (i) Q177, which is the residue which interacts most directly with the ligand, (ii) Q177, I231, A233, which constitute the three residues at the tope end of the active site which most directly effect ligand entry and (iii) Q1777, I231, A233, I180, E226, I227 constituting all of the distinct residues in the binding pocket. Therefore the following mutants were constructed as described below: (i) Q177Y, (ii) Q177Y, I231V, A233M and (iii) Q177Y, I231V, A233M, I180V, E226A and I227V. These amino acid changes were expected to confer potencies closer to those observed for the human enzyme. In addition, it was expected that mice genetically modified to carry these mutations would respond to inhibitors that are highly potent against the human enzyme but weakly potent versus the mouse enzyme.

Non-human, gene-targeted animal models useful for screening drugs or candidate drugs are provided. The animals have a genetically altered endogenous 11βHSD gene, such that the activity of the mutant 11βHSD1 is modulated. In contrast to previous gene-targeted animal models, the genetically altered 11βHSD1 gene in gene-targeted animals described herein is under endogenous transcriptional control and tissue-specific expression. Thus, the genetically altered endogenous 11βHSD1 gene is expressed in a normal manner, e.g., developmental, tissue-specific, and temporal (age-dependent) expression are the same as with the wild-type 11βHSD1 gene, and any species-specific effects seen with previous 11βHSD1 gene-targeted animals are avoided.

The subject animals are useful for identifying agents that modulate 11βHSD1 activity. Compounds will interact with 11βHSD1 selectively, and thus will affect only the 11βHSD1 isoform. The animals are also useful for testing the efficacy of drugs that modulate 11βHSD1 activity in treating 11βHSD1-related metabolic disorders, for example, obesity, dyslipidemia and diabetes.

Based on the comparison between the human and mouse 11βHSD1 structures, three mutation sites in mouse 11βHSD1 were selected for creating a humanized construct: Q177Y, I231V, and A233M. Two humanized constructs were prepared comprising either the single mutant Q177Y or the triple mutant Q177Y, I231V, A233M. A construct comprising the hexamutant Q177Y, I180V, E226A, I227V, I231V, A233M was also generated. Microsomes derived from HEK cells transfected with these constructs were first tested to confirm the retention of enzymatic function of the mutant proteins. These preparations where further tested to analyze the effect of the mutations on the activity of inhibitors covering a range of chemotypes.

Both the single-mutant and triple-mutant constructs were found to improve the potencies of most non-TZP compounds.

Gene-Targeted Non-Human Animals

Described and claimed herein are gene-targeted non-human animals that comprise a genetically altered endogenous 11βHSD1 gene (SEQ ID NO:1), wherein the genetically altered 11βHSD1 gene encodes a recombinant mutant 11βHSD1 protein that is inhibited by compounds that inhibit wild-type human 11βHSD1 (SEQ ID NO:1).

The minimum essential elements for inhibition correspond to three amino acids in the active site of 11βHSD1, specifically Tyrosine-177, Valine-231 and Methione-233. Thus, any genetic modification of the endogenous mouse 11βHSD1 gene that results in Tyrosine-177, Valine-231 and Methionine-233 substitutions is suitable for generating a gene-targeted non-human animal. The amino acid sequence of 11βHSD1 from the mouse contains a Glutamine-177, an Isoleucine-231 and an Alanine-233 that are in equivalent locations in the human enzyme. Weisgraber (1994) Adv. Protein Chem. 45:249-302. Thus, mutations at amino acids 177, 231 and 233 in the mouse results in a recombinant mutant 11βHSD1 that is inhibited by human 11βHSD1 inhibitory compounds.

In generating a non-human gene-targeted animal, a transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like.

Gene-targeted animals comprise a genetically altered endogenous 11βHSD1 gene that comprises a heterologous nucleic acid sequence that replaces a portion of the endogenous 11βHSD1 gene, which heterologous nucleic acid is stably integrated in all or a portion of the cells of the animal, especially in germ cells. Unless otherwise indicated, it will be assumed that a gene-targeted animal comprises stable changes to the germline sequence. During the initial generation of the gene-targeted animal, "chimeras" or "chimeric animals" are generated, in which only a subset of cells have the altered genome. Chimeras are primarily used for breeding purposes in order to generate the desired gene-targeted animal. Animals having a heterozygous alteration are generated by breeding of chimeras. Male and female heterozygotes are typically bred to generate homozygous animals. Of interest are gene-targeted mammals, e.g. cows, pigs, goats, non-human primates, horses, etc., and particularly rodents, e.g. rats; mice, etc.

The gene-targeted animals disclosed and claimed herein comprise a genetic modification in one or both alleles of the endogenous 11βHSD1 gene, e.g., gene-targeted animals described herein include both heterozygotes and homozygotes for the genetically modified 11βHSD1 gene.

The endogenous 11βHSD1 gene is a wild-type gene, and is under transcriptional control of endogenous control elements, e.g., control elements that are normally associated with an endogenous 11βHSD1 gene in a wild-type animal of the same species. Endogenous control elements include enhancers, elements that provide for tissue-specific expression of the endogenous 11βHSD1 gene, promoter elements, and the like.

Targeting Constructs

The introduced heterologous nucleic acid molecule undergoes homologous recombination with the endogenous 11βHSD1 gene of the species, and changes the endogenous 11βHSD1 gene to a mutant 11βHSD1 gene that encodes a mutant 11βHSD1 polypeptide which responds to human 11βHSD1 inhibitor compounds. Any modification that results in a mutant 11βHSD1 gene that encodes a mutant 11βHSD1 protein whose activity is modulated by compounds that modulate human 11βHSD1 is suitable.

In one embodiment, the targeting construct changes amino acid 177 to a tyrosine. In another embodiment, the targeting construct changes amino acid 231 to a valine. In another embodiment, the targeting construct changes amino acid 233 to a methionine. In further embodiments, the targeting construct changes amino acid 177 to a tyrosine, amino acid 231 to a valine, and amino acid 233 to a methionine. The mutated codon may be flanked (i.e., may have additional genomic DNA on the 5' and the 3' side of) by about 100 nucleotide (nt) to about 10 kb, by about 200 nt to about 8 kb, by about 400 nt to about 4 kb, or by about 500 nt to about 2 kb of genomic DNA.

Methods for generating mutations are well known in the art; any known method can be used to generate the targeting constructs described herein. Examples of protocols for site specific mutagenesis may be found in Gustin et al. (1993) Biotechniques 14:22; Barany (1985) Gene 37:111-23; Colicelli et al. (1985), Mol. Gen. Genet. 199:537-9; and Prentki et al. (1984), Gene 29:303-13. Methods for site specific mutagenesis can be found in Sambrook et al., Molecular Cloning: A Laboratory Manual, CSH Press 1989, pp. 15.3-15.108; Weiner, et al., (1993) Gene 126:35-41; Sayers et al., (1992) Biotechniques 13:592-6; Jones, et al., (1992) Biotechniques 12:528-30; Barton et al., (1990) Nucleic Acids Res 18:7349-55; Marotti, et al., (1989) Gene Anal. Tech. 6:67-70; and Zhu (1989) Anal Biochem 177:120-4.

If desired, the introduced mutation can, in addition to changing a specific amino acid codon, provide for a restriction endonuclease recognition sequence not present in the endogenous 11βHSD1 gene. Such a restriction site can be used to determine whether a cell comprises a genetically modified 11βHSD1 gene.

In one particular embodiment, a construct as described in Example 1 is used. This construct contains an insert comprising mouse 11βHSD1 which was altered to change glutamine 177 to a tyrosine (Q177Y), isoleucine 231 to a valine (I231V) and alanine 233 to a methionine (A233M) (SEQ ID NO:11). The encoded amino acid sequence for this triple mutant construct comprises SEQ ID NO:12. When this construct is used to replace the corresponding portion of the endogenous mouse 11βHSD1 gene, the activity of the recombinant mutant 11βHSD1 is modulated in response to human 11βHSD1 modulating compounds.

Whether a given construct will replace a portion of an endogenous 11βHSD1 gene such that the 11βHSD1 polypeptide encoded is responsive to human 11βHSD1 modulating compounds can be determined before making a gene-targeted animal with the construct. This can be achieved by first introducing the construct into a cell line and selecting for cells in which homologous recombination has occurred. Whether the recombinant 11βHSD1 produced by these cells are responsive to human 11βHSD1 inhibitor compounds can be determined by assays described herein.

DNA constructs for homologous recombination will comprise at least a portion of the 11βHSD1 gene with the desired genetic modification, and will include regions of homology to the target endogenous 11βHSD1 locus. Conveniently, markers for positive and negative selection are included. Methods for generating cells having targeted gene modifications through homologous recombination are known in the art. For various techniques for transfecting mammalian cells, see Keown et al. Methods in Enzymology 185:527-537 (1990).

Generating a Gene-Targeted Animal

As discussed herein, nucleic acids which encode 11βHSD1 or its modified forms can also be used to generate either transgenic animals or gene targeted animals, e.g., "knock-in" animals, which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding 11βHSD1 can be used to clone genomic DNA encoding both mouse and human 11βHSD1 in accordance with established techniques and the genomic sequences used to generate transgenic animals that contain cells which express DNA encoding mutant 11βHSD1. A portion of the genomic DNA encoding mouse 11βHSD1 can be deleted or replaced with a portion of the human 11βHSD1 gene, as well as a gene encoding a selectable marker which can be used to monitor integration.

Methods for generating transgenic animals, particularly animals such as mice or rats, have become conventional in the art and are described, for example, in U.S. Pat. Nos. 4,736,866 and 4,870,009. Typically, particular cells would be targeted for 11βHSD1 transgene incorporation with tissue-specific enhancers, for example, adipose cells or hepatic cells. Transgenic animals that include a copy of a transgene encoding mutant 11βHSD1 introduced into the germ line of the animal at an embryonic stage can be used to examine the effect of increased expression of DNA encoding mutant 11βHSD1. Such animals can be used as tester animals for reagents thought to confer protection from, for example, pathological conditions associated with an increase in its activity (e.g., an increase in cortisol production). In accordance with this facet of the subject matter described herein, an animal is treated with the reagent and a reduced incidence of the pathological condition (e.g., a decrease in cortisol production), compared to untreated animals bearing the transgene, would indicate a potential therapeutic intervention for the pathological condition.

Alternatively, mutant 11βHSD1 can be used to construct a 11βHSD1 gene targeted animal which has a mutant 11βHSD1 gene as a result of homologous recombination between the endogenous gene encoding 11βHSD1 and altered genomic DNA encoding mutant 11βHSD1 introduced into an embryonic stem cell of the animal. For example, cDNA encoding 11βHSD1 can be used to clone genomic DNA encoding both mouse and human 11βHSD1 in accordance with established techniques. Typically, several kilobases of unaltered flanking DNA (both at the 5' and 3' ends) are included in the vector (see e.g., Thomas and Capecchi, Cell, 51:503 (1987) for a description of homologous recombination vectors).

The vector is introduced into an embryonic stem cell line (e.g., by electroporation) and cells in which the introduced DNA has homologously recombined with the endogenous DNA are selected (see, e.g., Li et al., Cell, 69:915 (1992)). For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce gene-targeted animals. See U.S. Pat. Nos. 5,387,742; 4,736,866; and 5,565,186; and Larson et al. (2000) Mol. Ther. 2:631-639 for methods of making gene-targeted animals. Briefly, the selected cells are then injected into a blastocyst of an animal (e.g., a mouse or rat) to form aggregation chimeras (see, e.g., Bradley, in Teratocarcinomas and Embryonic Stem Cells: A Practical Approach, E. J. Robertson, ed. (IRL, Oxford, 1987), pp. 113-152). A chimeric embryo can then be implanted into a suitable pseudopregnant female foster animal and the embryo brought to term to create a gene targeted animal. Progeny harboring the homologously recombined DNA in their germ cells can be identified by standard techniques and used to breed animals in which all cells of the animal contain the homologously recombined DNA. If the gene alterations cause lethality at some point in development, tissues or organs can be maintained as allogeneic or congenic grafts or transplants, or in in vitro culture. Gene targeted animals can be characterized for instance, by their ability to respond to modulators of human 11βHSD1.

Isolated Cells

The subject matter described herein further provides cells isolated from a gene-targeted animal, particularly cells that synthesize mutant 11βHSD1 that respond to human 11βHSD1 inhibitors. The isolated cells are useful for testing agents for their ability to respond to human 11βHSD1 inhibitors. Cells are isolated using standard procedures. Cell lines may be derived from such isolated cells, and immortalized using standard techniques, e.g., through use of viruses. Of particular interest are cells derived from a gene-targeted animal that synthesize the mutant 11βHSD1 protein. In some embodiments, of particular interest are adipose cells or hepatic cells that produce the mutant 11βHSD1 protein. In other embodiments, cells derived from a gene-targeted animal are cells that respond to human 11βHSD1 inhibitors. Such cells include, but are not limited to, adipose cells, hepatic cells or lung cells or cell lines typically used to produce heterologous proteins such as human embryonic kidney 293 cells (HEK293), Chinese hamster ovary (CHO), and HeLa cells, as well as the 3T3-L1 adipocyte cell line.

Recombinant 11βHSD1 Protein

Further described herein are recombinant 11βHSD1 proteins, and compositions comprising a recombinant mutant 11βHSD1 protein. A recombinant 11βHSD1 protein is a mutant 11βHSD1 protein that has been modified such the recombinant 11βHSD1 protein is responsive to human 11βHSD1 inhibitors at improved potencies relative to the wild-type mouse 11βHSD1 protein. Recombinant 11βHSD1 protein can be used in screening assays to identify compounds that modulate recombinant 11βHSD1 activity, which agents are thus useful for treating 11βHSD1-associated metabolic disorders in humans, for example diabetes or metabolic syndrome.

Recombinant 11βHSD1 proteins comprise one or more amino acid substitutions compared to the 11βHSD1 polypeptide encoded by the endogenous 11βHSD1 gene of the gene-targeted animal from which they are derived. Thus, a recombinant 11βHSD1 polypeptide comprises the equivalents of human 11βHSD1 Tyr-177, Val-231 and Met-233, and, as a result, is responsive to human 11βHSD1 modulators at comparable potencies as would affect the wild-type human 11βHSD1 protein.

The recombinant 11βHSD1 protein disclosed and claimed herein is typically separated from its source, e.g., the gene-targeted animal, or the cell derived therefrom, or gene-targeted cell alone, that synthesize the recombinant protein. In certain embodiments, the subject proteins are present in a composition that is enriched for subject protein as compared to its source.

A mutant 11βHSD1 protein that responds to human 11βHSD1 modulator compounds may have one or more active site amino acid substitutions, insertions, and deletions compared to the wild-type non-human 11βHSD1 protein, as long as the protein comprises the equivalents of human 11βHSD1 Tyr-177, Val-231, and Met-233, and, as a result, respond to human 11βHSD1 inhibitors. Accordingly, also provided are recombinant 11βHSD1 proteins that are substantially identical to the sequence of wild-type non-human 11βHSD1 polypeptide, whereby substantially identical is meant that the protein has an amino acid sequence identity of at least about 75%, at least about 80% at least about 85%, at least about 90%, at least about 95%, or at least about 98% to the sequence of wild-type non-human 11βHSD1 polypeptide.

The subject proteins and polypeptides may be obtained from a gene-targeted animal, a cell derived from a gene-targeted animal, a cell expressing a gene targeted to that specific cell. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Nucleic Acid Molecules and Host Cells

Further described herein are nucleic acid molecules comprising a nucleotide sequence that encodes a recombinant 11βHSD1 protein, as well as host cells comprising the nucleic acid molecules. The subject nucleic acid molecules may be part of a vector ("construct") for use in generating a gene-targeted animal, as described above. In addition, a nucleic acid molecule described herein may encode all or part of a recombinant 11βHSD1 polypeptide, and is useful as part of an expression vector to produce recombinant 11βHSD1 polypeptide.

Further described are nucleic acid molecules comprising one or more exons and one or more introns of an 11βHSD1 gene, wherein the 11βHSD1 gene is a non-human 11βHSD1 gene, and the 11βHSD1 gene is modified such that the 11βHSD1 protein encoded thereby is responsive to human 11βHSD1 modulator compounds, for example an 11βHSD1 inhibitor. In some embodiments, a subject nucleic acid molecule comprises a mutant 11βHSD1 gene, wherein an exon comprising a codon for Gln-177 is modified to encode tyrosine (SEQ ID NO:5). In some embodiments, a subject nucleic acid molecule comprises a mutant 11βHSD1 gene, wherein an exon comprising a codon for Ile-231 is modified to encode valine (SEQ ID NO:7). In some embodiments, a subject nucleic acid molecule comprises a mutant 11βHSD1 gene, wherein an exon comprising a codon for Ala-233 is modified to encode methionine (SEQ ID NO:9). In some embodiments, a subject nucleic acid molecule comprises a mutant 11βHSD1 gene, wherein an exon comprising a codon for Gln-177 is modified to encode tyrosine, an exon comprising a codon for Ile-231 is modified to encode valine and an exon comprising a codon for Ala-233 is modified to encode methionine (SEQ ID NO:11). The sequences of the 11βHSD1 gene from a number of species are known and are publicly available. The sequence of the mouse 11βHSD1 gene is found under Genbank accession number DQ089001. The sequence of the human 11βHSD1 gene is found under Genbank accession number NM_005525

In some embodiments, nucleic acids described herein include the open reading frame encoding all or part of the recombinant 11βHSD1 polypeptide, one or more introns, may further include adjacent 5' and 3' non-coding nucleotide sequences involved in the regulation of expression, and are generally up to about 10 kb in total length, but possibly longer. The DNA sequences encoding all or part of the recombinant 11βHSD1 are genomic DNA or a fragment thereof. The recombinant 11βHSD1 gene may be introduced into an appropriate vector for extrachromosomal maintenance or for integration into the host.

A genomic sequence of interest comprises the mutant 11βHSD1 nucleic acids present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where 11βHSD1 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al Mol Med 1:194-205 (1995); Mortlock et al. Genome Res. 6:327-33 (1996); and Joulin and Richard-Foy Eur J Biochem 232:620-626 (1995).

The regulatory sequences may be used to identify cis acting sequences required for transcriptional or translational regulation of 11βHSD1 expression, especially in different tissues or stages of development, and to identify cis acting sequences and trans acting factors that regulate or mediate expression. Such transcription or translational control regions may be operably linked to an 11βHSD1 gene in order to promote expression of wild type or altered 11βHSD1 or other proteins of interest in cultured cells, or in embryonic, fetal or adult tissues; and for gene therapy.

In other embodiments, a nucleic acid molecule comprises sequences that encode all or part of a mutant 11βHSD1 protein. In one embodiment, the mutant 11βHSD1 encoding nucleic acid comprises a portion of mouse genomic DNA as well as a portion of human genomic DNA. In another embodiment, the mutant 11βHSD1 encoding nucleic acid comprises both genomic DNA and cDNA. The nucleic acid compositions may encode all or a part of the 11βHSD1 polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, e.g. greater than 100 nt are useful for production of the encoded polypeptide. For use in amplification reactions, such as PCR, a pair of primers will be used.

Subject nucleic acid molecules may comprise other, non-recombinant 11βHSD1 nucleic acid molecules ("heterologous nucleic acid molecules") of any length. For example, the subject nucleic acid molecules may be flanked on the 5' and/or 3' ends by heterologous nucleic acid molecules of from about 1 nt to about 10 nt, from about 10 nt to about 20 nt, from about 20 nt to about 50 nt, from about 50 nt to about 100 nt, from about 100 nt to about 250 nt, from about 250 nt to about 500 nt, or from about 500 nt to about 1000 nt, or more in length. For example, when used as a probe to detect nucleic acid molecules capable of hybridizing with the subject nucleic acids, the subject nucleic acid molecules may be flanked by heterologous sequences of any length.

The subject nucleic acid molecules may also be provided as part of a vector, a wide variety of which are known in the art and need not be elaborated upon herein. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

The subject nucleic acid molecules are isolated and obtained in substantial purity, generally as other than an intact chromosome. Usually, the DNA will be obtained substantially free of other nucleic acid sequences that do not include a sequence or fragment thereof of the subject genes, generally being at least about 50%, usually at least about 90% pure and are typically "recombinant", e.g. flanked by one or more nucleotides with which it is not normally associated on a naturally occurring chromosome.

The subject nucleic acid compositions find use in the preparation of all or a portion of the recombinant 11βHSD1 polypeptides described herein, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, e.g. increased protein synthesis, stability, reactivity with defined antisera, an enzyme marker, e.g. β-galactosidase, etc.

Proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. adipose cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequences of the subject proteins may be used to identify and investigate parts of the protein important for function.

Specific expression systems of interest include bacterial, yeast, insect cell and mammalian cell derived expression systems. A wide variety of such systems are known to those or ordinary skill in the art.

Recombinant host cells comprising a subject nucleic acid molecule may serve as a source of recombinant 11βHSD1 protein as described herein. They may also serve in drug screening assays to identify agents that modulate 11βHSD1 activity after dosage with human 11βHSD1 modulating compounds. In some embodiments, of particular interest are mammalian cells that normally produce 11βHSD1. Examples of such cells include adipose cells, hepatic cells and lung cells.

Drug Screening Assays

Additional embodiments described herein include methods for identifying agents that modulate 11βHSD1 activity, using a gene-targeted animal, or isolated cell, or isolated mutant 11βHSD1 protein. In some embodiments, the methods identify agents that affect a phenomenon associated with an 11βHSD1-associated metabolic disorder, such as metabolic syndrome or diabetes. The methods generally comprise contacting a gene-targeted animal or isolated cell/cell line (e.g., HEK293, 3t3-L1, CHO) with a test agent, and determining the effect of the agent on the gene-targeted animal, the isolated cell, or mutant 11βHSD1 produced by an isolated cell. Agents that modulate 11βHSD1 activity are identified by a change in an activity associated with 11βHSD1 which includes, but is not limited to, cortisol production.

An effect on 11βHSD1 activity, or any associated phenomenon (e.g., a metabolic disorder or a symptom of a metabolic disorder) or any 11βHSD1-associated activity, can be determined in comparison to a suitable control. Suitable controls for assays using a gene-targeted animal described herein include a wild-type animal of the same species contacted with the test agent; and a gene-targeted animal not contacted with the test agent. Suitable controls for assays using a cell isolated from a gene-targeted animal described herein include a cell not contacted with the test agent; and a cell of the same cell type from a wild-type animal of the same species, which cell is contacted with the test agent. Controls for specificity of the test agent on mutant 11βHSD1 polypeptide include controls which assay the effect of the test agent on another human 11βHSD1 isoform, e.g., human 11βHSD2; and controls which assay an activity of the mutant 11βHSD1 protein in the absence of the test agent.

A wide variety of assays may be used for this purpose, including assays which measure product produced from a suitable substrate. Examples include but are not limited to; cortisol production from exogenously supplied cortisone or corticosterone production from exogenously supplied 11-dehydrocorticosterone. The substrate may be administered in a radiolabeled form or non-radiolabeled form depending upon the analytic methods used to detect the formation of product.

Depending on the particular assay, whole animals may be used, or cells derived therefrom, or isolated mutant 11βHSD1 protein. Cells may be freshly isolated from an animal, or may be immortalized in culture. Any cell that produces mutant 11βHSD1 can be used, e.g., adipose cells. Cells of particular interest include adipose tissue or hepatic tissue of gene-targeted animals described herein.

The term "agent" as used herein describes any molecule, e.g. protein or non-protein organic pharmaceutical, with the capability of affecting any of the biological actions of 11βHSD1. Agents of particular interest are those that modulate 11βHSD1 activity. Generally a plurality of assay mixtures are run in parallel with different agent concentrations to obtain a differential response to the various concentrations. Typically, one of these concentrations serves as a negative control, e.g. at zero concentration or below the level of detection.

Candidate agents encompass numerous chemical classes, though typically they are organic molecules, e.g., small organic compounds having a molecular weight of more than 50 and less than about 2,500 daltons. Candidate agents comprise functional groups necessary for structural interaction with proteins, e.g., van der Waals interactions and hydrogen bonding, and may include at least an amine, carbonyl, hydroxyl or carboxyl group, and may include at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design. Candidate agents for treating metabolic disorders can be screened for their ability to modulate 11βHSD1 function. Efficacious candidates can be identified by phenotype, e.g. a decrease in cortisol production between wild-type animals and a gene-targeted animal such as those described herein.

Agents that have an effect in an assay method described herein may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barriers.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Samples derived from a gene-targeted animal such as those described herein may also be used in assays. Samples, as used herein, include biological fluids such as tracheal lavage, blood, cerebrospinal fluid, tears, saliva, lymph, dialysis fluid and the like; organ or tissue culture derived fluids; and fluids extracted from physiological tissues. Also included in the term are derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

For example, detection may utilize staining of cells or histological sections, performed in accordance with conventional methods. Antibodies to mutant 11βHSD1 may be added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method depends on the in vitro detection of binding between antibodies and 11βHSD1 in a lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods described herein. The binding agent may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

11βHSD1-Associated Activity

Disclosed and claimed herein are assays for measuring 11βHSD1-associated activity, and include, but are not limited to, measuring cortisol or corticosterone production. Such assays typically involve contacting a mutant 11βHSD1 protein with a test agent, to form a sample, and determining the effect, if any, of the agent on cortisol production. Modulatory compounds may be added to the assay if so desired.

Analysis of Mutant 11βHSD1 Expression

One method for detecting mutant 11βHSD1 expression is to quantitate mRNA levels. mRNA can be isolated by the acid guanidinium thiocyanate phenol:chloroform extraction method (Chomczynski et al., Anal Biochem 162:156-159 (1987)) from cell lines and tissues of gene-targeted animals to determine expression levels by Northern blots. Whether a mutant 11βHSD1 gene is expressed can be determined using, e.g., a labeled oligonucleotide probe that spans the on of the active site mutations. For example, the labeled oligonucleotide may comprise the mutation that led to the Glu-177 substitution, in which case expression of the genetically modified gene is identified by hybridization with the labeled probe.

A second method for analyzing mRNA expression is by in situ hybridization whereby radioactive or enzymatically labeled probes can be used to detect mRNA in situ. The probes are degraded approximately to 100 nucleotides in length for better penetration of cells. The procedure of Chou et al. J Psychiatr Res 24:27-50 (1990) for fixed and paraffin embedded samples is briefly described below although similar procedures can be employed with samples sectioned as frozen material.

Paraffin slides for in situ hybridization are dewaxed in xylene and rehydrated in a graded series of ethanols and finally rinsed in phosphate buffered saline (PBS). The sections are postfixed in fresh 4% paraformaldehyde. The slides are washed with PBS twice for 5 minutes to remove paraformaldehyde. Then the sections are permeabilized by treatment with a 20 μg/ml proteinase K solution. The sections are refixed in 4% paraformaldehyde, and basic molecules that could give rise to background probe binding are acetylated in a 0.1 M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

Mutant 11βHSD1 expression can also be detected by examining protein expression is through Western blot analysis whereby protein fractions can be isolated from tissue homogenates and cell lysates and subjected to Western blot analysis as described by Harlow et al., Antibodies: A laboratory manual, Cold Spring Harbor, N.Y., (1988); Brown et al., J. Neurochem 40:299-308 (1983); and Tate-Ostroff et al., Proc Natl Acad Sci 86:745-749 (1989)). Only a brief description is given below.

The protein fractions can be denatured in Laemmli sample buffer and electrophoresed on SDS-polyacrylamide gels. The proteins are be then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of 11βHSD1 proteins. An antibody that distinguishes between an 11βHSD1 polypeptide having Tyr-177 from one having Gln-177 may be employed.

Another method of detecting mutant 11βHSD1 expression is by isoelectric focusing combined with western blot analysis. As a result of the glutamine to tyrosine substitution, for example, a mutant 11βHSD1 protein may have a different charge than the wild-type protein. Therefore, isoelectric focusing can be used to distinguish between wild-type and recombinant 11βHSD1 proteins. Protein fractions are isolated as described above, and subjected to isoelectric focusing, as described in the Examples, using standard techniques. Isoelectric focusing is generally performed using ampholines, typically in a pH range of 4-7, on polyacrylamide gels (or other suitable matrix), in the presence of 6 M urea.

11βHSD1-Related Metabolic Disorders

Gene-targeted animals described herein can be used to screen agents for their ability to treat diabetes and other 11βHSD1-related disorders, for example, metabolic syndrome or diabetes, obesity, atherosclerosis, hypertension, dyslipidemia, hypertriglyceridemia, hypercholesterolemia, osteoporosis, inflammatory disease, rheumatoid arthritis, osteoarthritis, inflammatory bowel disease, Crohn's disease, and cognitive disorders.

A gene-targeted animal described herein can be used to test agents for an effect on serum cholesterol levels. In these embodiments, the methods comprise contacting a gene-targeted animal with a test agent, and determining the effect, if any, on serum cortisol levels. A reduction in serum cholesterol level, when compared with an effect of the agent on a control animal, indicates that the agent is effective in reducing serum cholesterol levels. Gene-targeted animals described herein can also be used to test agents for an effect on a disease associated with diabetes, e.g., hypertension.

Therapeutic Agents

The subject matter described herein provides agents identified using the methods described herein. Agents that modulate 11βHSD1 activity are used to treat 11βHSD1-related disorders. An effective amount of the active agent is administered to the host, where "effective amount" means a dosage sufficient to produce a desired result. Generally, the desired result is a reduction in enzymatic activity of a subject therapeutic agent as compared to a control.

Formulations, Dosages, and Routes of Administration

Further described are formulations, including pharmaceutical formulations, comprising an agent that modulates 11βHSD1 activity. In general, a formulation comprises an effective amount of an agent that modulates 11βHSD1 activity. An "effective amount" means a dosage sufficient to produce a desired result, e.g., reduction in 11βHSD1 activity. Generally, the desired result is at least a reduction in cortisol levels.

Formulations

In the subject methods, the active agent(s) may be administered to the host using any convenient means capable of resulting in the desired modulation of 11βHSD1 activity.

Thus, the agent can be incorporated into a variety of formulations for therapeutic administration. More particularly, the agents described herein can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds described herein can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds described herein can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds described herein calculated in an amount sufficient to produce the desired effect in association with a pharmaceutically acceptable diluent, carrier or vehicle. The specifications for the novel unit dosage forms of the subject matter described herein depend on the particular compound employed and the effect to be achieved, and the pharmacodynamics associated with each compound in the host.

Other modes of administration will also find use with the subject matter described herein. For instance, an agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject proteins by the nasal mucosa.

An agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that reduces 11βHSD1 domain interaction and can be administered in a single dose. Alternatively, a target dosage of an agent that modulates 11βHSD1 activity can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that modulates 11βHSD1 activity is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, e.g., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an 11βHSD1-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

EXAMPLES

The following examples provide those of ordinary skill in the art with a complete disclosure and description for making and using the subject matter described and claimed herein. These examples are neither intended to limit the scope of what the inventors regard as their invention nor are they intended to represent that the experiments presented are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Generation of Mutant Constructs

Generation of 11βHSD1 Clone in pcDNA3.1 (pcDNA3.1DmHSD1WT)

The full length mouse 11βHSD1 coding sequence was originally cloned from Invitrogene's mouse cDNA library and was delivered in a pDEST26 vector, designated pDEST26 mHSD1. Its sequence matched Genbank entry DQ089001.

A polymerase chain reaction (PCR) was carried out with two primers, mHSD1-ATG (5'-CACCATGGCAGTTAT-GAAAAATT) (SEQ ID NO:15) and mHSD1-STOP (5'-CTAGTTACTTACAAACATGTCCTT) (SEQ ID NO:16) using pDEST26 mHSD1 as the template. Stratagene's Pfu-Turbo® hotstart DNA polymerase, a special formulation of cloned Pfu DNA polymerase originally from *Pyrococcus furiosus*, was used for PCR amplification. The PCR reaction contained 1 μL (2.5 U) of PfuTurbo® hotstart DNA polymerase, 5 μL of 10×Pfu buffer supplied from Stratagene, 1.5 μL of 10 mM dNTP (Invitrogen), 36.5 μL of water, 2.5 μL of 10 μM mHSD1-ATG, 2.5 μL of mHSD1-STOP primers and 10 ng pDEST26 mHSD1 DNA. The PCR reaction conditions were as follows: one cycle at 94.5° C. for 2 minutes to denature the DNA, twenty-five cycles of the amplification step (94.5° C. for 30 seconds; 56° C. for 45 seconds, followed by 72.0° C. for 1.5 minutes) and one cycle at 72° C. for 10 minutes to complete amplification. The PCR reaction products were run on a 1.2% agarose gel and the band corresponding to the expected 879 base pair insert was cut out and purified. After purification, the PCR fragment was cloned into the 5514 base pair linear pcDNA3.1D/V5-His-TOPO vector. (Invitrogen, Carlsbad, Calif.). The clones were then screened by digestion with HindIII. Clones with the correct insert generated two fragments of 5680 and 737 base pairs upon digestion with HindIII. The clone's sequence was confirmed and was designated as pcDNA3.1DmHSD1WT.

Generation of Triple Mutant 11βHSD1 Using pcDNA3.1DmHSD1WT

Site-Directed mutagenesis was used to make three point mutations in 11βHSD1 (Stratagene's QuikChange II XL, Stratagene, La Jolla, Calif.). The pcDNA3.1DmHSD1WT vector described in Example 1 was used as the template. The following mutations were made: glutamine 177 was changed to tyrosine (Q177Y), isoleucine 123 was changed to valine (I231V) and alanine 233 was changed to methionine (A233M). The following two primers were designed to mutate the three amino acids:

| Mutation | Mutant Primer Sequence |
|---|---|
| Q177Y | 5'-GGCTGGGAAAATGACCT ATCCTATGATTGCTCCC (SEQ ID NO: 17) |
| I231V | 5'-CAGCTATGAAGGAAATCTCTGGGATAGTTAACATGCAAGC TTCT CCC (SEQ ID NO: 18) |
| A233M | 5'-CAGCTATGAAGGAAATCTCTGGGATAGTTAACATGCAAGC TTCT CCC (SEQ ID NO: 19) |

The PCR amplification was carried out with 1 μL Primer 1 (100 ng/μL), 2 μL Primer 2 (100 ng/μL), 2.5 μL 10× QuikChange Multi reaction buffer, 0.75 μL QuikSolution, 1 μL dNTP Mix, 1 μL QuikChange Multi Enzyme Blend, 1 μL pcDNA3.1DmHSD1WT (150 ng/μL) and 15.75 μL water. The PCR conditions were: one cycle at 95° C. for 1 minute to denature the DNA followed by thirty cycles of the amplification step (95° C. for 1 minute; 55° C. for 1 minute and 65° C. for 14 minutes). The remainder of the procedure was followed exactly as described by the manufacturer. Clone candidates were first screened with BamHI/HpaI. The I231V mutation generated a HpaI site, so the candidates would yield a 711 base pair HpaI fragment. The clones shown to contain the HpaI restriction site were then sequenced to confirm the three mutations. The confirmed clone was named pcDNA3.1DmHSD1-3M.

Generation of the Wild Type 11βHSD1 and Triple Mutant of 11βHSD1 with C-Terminal Flag Tag In order to quantitate protein expression using an anti-Flag tag antibody, a Flag tag (5'-TCAGTCGTCATCGTCCTTG-TAGTCCATGTTACTTAC AAACATGTCCTT) (SEQ ID NO:20) was added onto the C-terminus of the 11βHSD1 coding sequence in vectors pcDNA3.1DmHSD1WT and pcDNA3.1DmHSD1-3M by substituting the wild type 11βHSD1 fragment into a pcDNA3.1Dh-mChimCF plasmid that contained a C-terminal Flag tag. The chimeric mouse-human 11βHSD1 enzyme is expressed by the pcDNA3.1Dh-mChimCF vector which consists of a mouse 11βHSD1 clone that has amino acids 175-233 substituted with the corresponding human 11βHSD1 DNA fragment (GenScript Corp, Piscataway, N.J.) and the Flag tag.

There were two HindIII sites in all of the above clones: the first site was located in the 5' end of the multi cloning sites of pcDNA 3.1D and the second site was located at amino acid 234 on mouse 11βHSD1. Since all of the mutations were within this HindIII fragment, the fragment was removed from the human-mouse chimera (the pcDNA3.1Dh-mChimCF plasmid) by HindIII digestion and replaced with the corresponding HindIII fragment from pcDNA3.1DmHSD1WT in order to generate the pcDNA3.1DmHSD1WT-CF. This same strategy was used with the fragment from pcDNA3.1DmHSD1-3M in order to generate the pcDNA3.1DmHSD1-3M-CF. Therefore, all three clones were digested by HindIII enzyme and the digestion products were run in a 0.8% agarose gel to separate the two fragments of each clone. The large HindIII-HindIII fragment from the pcDNA3.1Dh-mChimCF clone, which contained the pUC57 vector with the 3' end of the mouse 11βHSD11 (amino acids 235 to 292), as well as the C-Flag tag, was purified as the vector for the generation of both new clones. Then the smaller HindIII-HindIII fragments from both pcDNA3.1DmHSD1WT and pcDNA3.1DmHSD1-3M that contained the majority of the mouse 11βHSD1 gene (amino acids 1 to 234) were purified as inserts. Each of these inserts was then ligated into pcDNA3.1Dh-mChimCF separately to obtain pcDNA3.1DmHSD1WT-CF and pcDNA3.1DmHSD1-3M-CF. Clones were screened with AlwNI/XhoI. Positive clones were confirmed by nucleotide sequencing.

Transient Transfection of the Triple Mutant

ATCC HEK-293 (CRL-1573), a hypotriploid human cell line, was used for transient expression of the proteins of interest. Cells were grown at 37° C. with 5% $CO_2$ in DMEM medium (Invitrogen, Carlsbad, Calif.) with 10% Fetal Bovine Serum, 1 mM Sodium Pyruvate, 0.1 mM Non-Essential Amino Acids, 2 mM GluMAX and 1× Antibiotic-Antimycotic (all Invitrogen). Maxiprep DNAs for the transient transfections were prepared using Qiagen's Qiafilter Plasmid Maxi Kit (Qiagen, Valencia, Calif.). DNA quantities and qualities were determined by Varian's Cary UV-Visible Spectrophotometer. The Invitrogen transfection kit Lipofectamine™ 2000 was used for transfection and the kit protocol was followed exactly as described by the manufacturer as follows. Approximately 18 hours before the transfection, HEK-293 cells were seeded into T-150 flasks in the same growth media as above but without antibiotics. On the day of transfection, the cells were approximately 80-90% confluent. For each T-150 flask, 60 μg DNA in 3.75 ml Opti-DMEM was added to one 50 ml tube and 150 μl Lipofectamine™ 2000 in 3.75 ml Opti-DMEM was added to a second 50 ml tube. The tubes were left at room temperature for 5 minutes, then gently mixed and incubated for 20 minutes at room temperature. The mixture was then added to the T-150 flask with cells and growth medium. The flasks were incubated overnight. The transfection medium was removed and 30 ml of regular growth medium was added. On the third day after transfection (~46 hrs later), the cells were washed once with 15 ml PBS buffer and then another 10 ml PBS was used to wash the cells off the flask. Cells from two or three flasks were combined into one 50 ml tube and centrifuged at 350×g for ten minutes to generate cell pellets. The cell pellets were flash frozen in liquid N2 and stored at –80° C.

Example 2

Generation of Mutant Mice

Generation of the Insert (pUC57FA-3M) for Homologous Recombination

A strategy was developed for generating a "knock in" mouse carrying the triple mutant described above. A 2625 bp genomic DNA sequence containing the exons to be targeted for recombination in conjunction with the desired amino acid changes was designed and synthesized (Genescript Corp., Piscataway, N.J.). The synthetic fragment was delivered in a pUC57 vector and named pUC57FA-3M.

Example 3

Analysis of Triple Mutant Humanized 11βHSD1 Enzyme

The triple mutant construct was also used to assess potencies of several inhibitors that showed high potencies in the human enzyme. As shown in Table 1, many inhibitors showed enhanced activity in the humanized mouse enzyme with respect to the native form.

TABLE 1

11βHSD1 Variant IC50 values (nM) in Various Models

| Inhibitor number | Human | Mouse | mQ177Y | mQ177Y, I231V, A233M | mQ177Y, I180V, E226A, I227V I231V, A233M |
|---|---|---|---|---|---|
| 1 | 0.12 | 6320 | 222 | 599 | 5620 |
| 2 | 898 | 163 | 178 | 420 | 4400 |
| 3 | 7.8 | 309 | 14.4 | 45.5 | 435 |
| 4 | 5.5 | 46.7 | 19.5 | 5.2 | 2.0 |
| 5 | 77.5 | 213 | 29.0 | 56.7 | 132.5 |
| 6 | 108 | 1930 | 123 | 636 | 503 |
| 7 | 1130 | >30000 | 16500 | 583 | 289 |
| 8 | 6.9 | 4360 | 90.5 | 106 | 1280 |

** Bold values indicate >5 fold improvement over mouse wild-type 11βHSD1

Preparation of 11 β-HSD1 Microsomes

Frozen transfected HEK cells were transfected and resuspended in 1 ml of 50 mM Tris pH=7.5, 2 mM EDTA (assay buffer)+0.25M sucrose+protease inhibitor Cocktail 0.2% (sigma P 8340) per a T-150 flask. The cells were then homogenized with a polytron 3 times for 10 sec at 25,000 rpm with tubes placed on ice. The cells were then centrifuged for 10 min (2300 g, at 4° C.) and the supernatant was collected. The supernatant was then centrifuged in Ti 70.1 for 1 h (30,000 RPM 4° C.). The membrane pellet was then resuspended in 0.2 ml/flask of assay buffer+protease inhibitor Cocktail 0.2% W/O sucrose using polytron. The protein concentration was determined and the pellets were then frozen in 100 μl portions in –80 C.

Kinetic Characterization

The reactions consisted of 50 mM MES pH=6.5, 2 mM EDTA, BSA, 50 μg/ml, 200 μM NADPH, Cortisone and dehydroxycorticosterone (50-3200 nM) and 11 βHSD1 microsomes (3-600 μg/ml). Reactions were incubated for 1 h at RT and substrate conversion was maintained at ≤30%. After incubation was completed, the reactions were stopped by the addition of 100 μl acetonitrile containing internal standard (triamcinolone, 500 ng/ml), the plate was centrifuged to remove any particles (10 min, 1350×g) and the supernatant was transferred to a fresh plate for LC/MS analysis with the appropriate cortisol and corticosterone standards. $K_m$ and $V_{max}$ were determined based on the Michaelis-Menten equation $V=(V_{max}*[S])/(K_m+[S])$.

$IC_{50}$ Determinations

Reactions were set as above with cortisone concentration kept constant at 200 nM and the concentration 11βHSD1 microsomes concentration varying from 50 μg/ml to 600 μg/ml depending on mutant activity and maintaining cortisone conversion below 30%. The tested inhibitors (0.1 nM-30 μM) were diluted initially in DMSO, then into assay buffer, yielding a final DMSO concentration of 0.25% in the reaction. $IC_{50}$ values were calculated using $V=V_{min}+(V_{max}-V_{min})/(1+10\char`\^((Log\ IC50-Log\ [S])*n))$. In cases where inhibition was not complete at the highest inhibitor concentration tested, $V_{min}$ was fixed at 0. Results are reported in Table 1.

While the subject matter described herein has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 4

In Vivo Proof of Concept

As described above, a genetically modified mouse carrying three amino acid changes (Q177Y, I231V, A233M) in the 11βHSD1 gene was created. These mice are termed "triple mutant mice". In order to show that the triple mutant mice respond to compounds that are highly potent against the human enzyme but weakly potent against the mouse enzyme, the following study was performed.

Compound A has an $IC_{50}$ against the human 11βHSD1 enzyme of 4 nM. In contrast, the $IC_{50}$ against the mouse enzyme is 625 nM. This represents a potency separation of greater than 100 fold. Groups of C57Bl/6 wild type mice or C57Bl/6 triple mutant mice received a 10 mg/kg oral dose of Compound A in vehicle or the vehicle alone. One hour later, the animals received an oral dose of 11-dehydrocorticosterone (DHC), a substrate for 11βHSD1. Over the following 2 hours, plasma samples were obtained at various time points. The concentration of corticosterone, the product of the 11βHSD1 catalyzed reduction of DHC, were assayed by enzyme-linked immunosorbent assay. The plasma corticosterone concentration was plotted versus time and the area under the curve was calculated.

Figure 10:
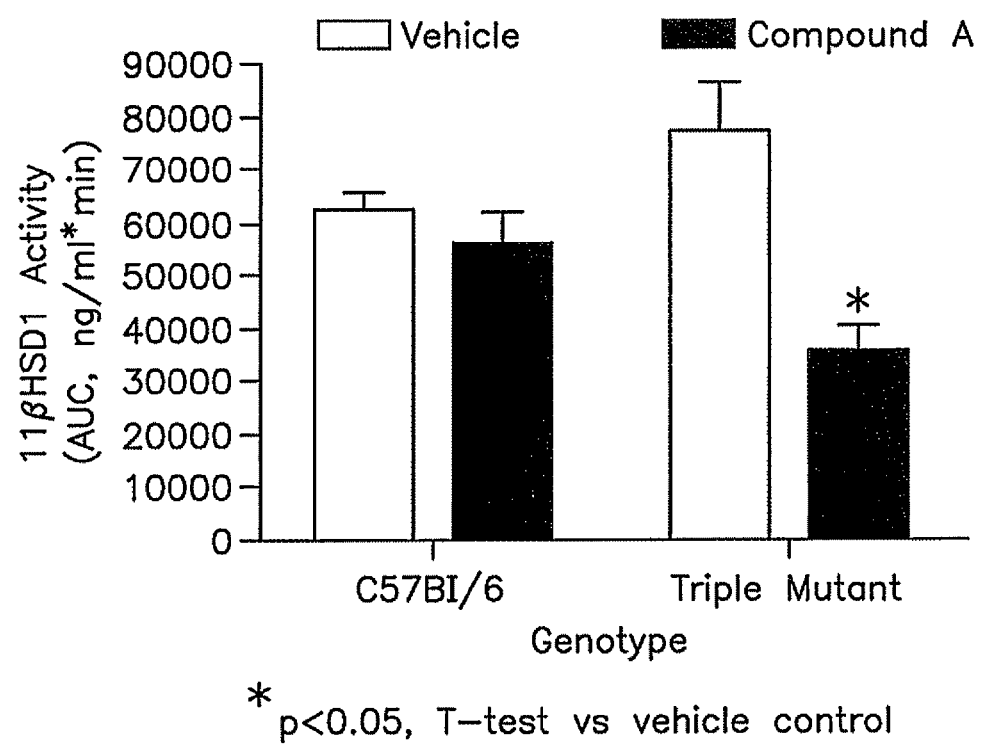
FIG. 10 represents the in vivo 11βHSD1 activity of Compound 2 in wild type C57Bl6 mice and mice with triple mutant inserted into 11βHSD1 gene via homologous recombination. Mice were treated with either vehicle or compound 2 by oral gavage. 11βHSD1 activity was monitored via conversion of exogenous 11-dehydrocorticosterone to corticosterone.

The graph in FIG. 10 shows that treatment of wild type C57Bl/6 mice with 10 mg/kg of Compound A did not reduce the 11βHSD1-mediated conversion of DHC to corticosterone. In contrast, treatment of triple mutant C57Bl/6 mice with 10 mg/kg of Compound A reduced the conversion of DHC to corticosterone by 52%. This result is indicative of the greater potency of Compound A against the triple mutant 11βHSD1 enzyme as compared to the wild type mouse enzyme. The concentration of Compound A was similar in both strains of mice.

These results prove the concept that conversion of 3 amino acid residues in the active site of the mouse enzyme to their human counterparts enables the demonstration of in vivo efficacy of compounds that are weakly potent against murine 11βHSD1 but highly potent against the human enzyme.

What is claimed is:

1. An isolated nucleic acid molecule encoding a polypeptide of SEQ ID NO: 6.

2. An isolated nucleic acid molecule encoding a polypeptide of SEQ ID NO: 12.

* * * * *

UNITED STATES PATENT AND TRADEMARK OFFICE
CERTIFICATE OF CORRECTION

PATENT NO. : 8,420,365 B2
APPLICATION NO. : 12/681916
DATED : April 16, 2013
INVENTOR(S) : David Gordon et al.

It is certified that error appears in the above-identified patent and that said Letters Patent is hereby corrected as shown below:

On the Title Page:

Item 56, column 2 (Other Publications), line 5, delete "Metaboic" and insert --Metabolic--, therefor.

In the Claims:

In Claim 1, column 51, line 9 (approx.), delete "a" and insert --the--, therefor.

In Claim 2, column 52, line 8 (approx.), delete "a" and insert --the--, therefor.

Signed and Sealed this
Fourth Day of March, 2014

Michelle K. Lee
*Deputy Director of the United States Patent and Trademark Office*